(12) United States Patent
Zhang et al.

(10) Patent No.: US 11,111,249 B2
(45) Date of Patent: Sep. 7, 2021

(54) HETEROARYL-PYRAZOLE DERIVATIVE, AND PREPARATION METHOD THEREFOR AND MEDICAL APPLICATION THEREOF

(71) Applicants: Jiangsu Hengrui Medicine Co., Ltd., Jiangsu (CN); Shanghai Hengrui Pharmaceutical Co., Ltd., Shanghai (CN)

(72) Inventors: Guobao Zhang, Shanghai (CN); Dianqiang Ma, Shanghai (CN); Huiqing Yuan, Shanghai (CN); Feng He, Shanghai (CN); Weikang Tao, Shanghai (CN)

(73) Assignees: Jiangsu Hengrui Medicine Co., Ltd., Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 16/612,620

(22) PCT Filed: May 17, 2018

(86) PCT No.: PCT/CN2018/087248
§ 371 (c)(1),
(2) Date: Nov. 11, 2019

(87) PCT Pub. No.: WO2018/210298
PCT Pub. Date: Nov. 22, 2018

(65) Prior Publication Data
US 2020/0131187 A1 Apr. 30, 2020

(30) Foreign Application Priority Data

May 18, 2017 (CN) .......................... 201710352719.5

(51) Int. Cl.
| | | |
|---|---|---|
| *A61K 31/519* | (2006.01) | |
| *A61K 31/4162* | (2006.01) | |
| *A61K 31/437* | (2006.01) | |
| *A61P 35/00* | (2006.01) | |
| *A61P 31/00* | (2006.01) | |
| *A61P 31/12* | (2006.01) | |
| *A61P 31/14* | (2006.01) | |
| *A61P 31/16* | (2006.01) | |
| *A61P 31/18* | (2006.01) | |
| *A61P 31/20* | (2006.01) | |
| *A61P 31/22* | (2006.01) | |
| *C07D 487/04* | (2006.01) | |
| *C07D 519/00* | (2006.01) | |

(52) U.S. Cl.
CPC ......... *C07D 487/04* (2013.01); *C07D 519/00* (2013.01)

(58) Field of Classification Search
CPC .............. A61K 31/519; A61K 31/4162; A61K 31/437; A61P 35/00; A61P 31/00; A61P 31/12; A61P 31/14; A61P 31/16; A61P 31/18; A61P 31/20; A61P 31/22; C07D 487/04

See application file for complete search history.

(56) References Cited

U.S. PATENT DOCUMENTS

2011/0046369 A1 2/2011 Hashimoto et al.
2015/0266883 A1 9/2015 Coe et al.

FOREIGN PATENT DOCUMENTS

| CN | 104507939 B | 4/2015 |
|---|---|---|
| CN | 104780924 B | 9/2016 |
| CN | 106661034 B | 11/2019 |
| WO | 0212224 A1 | 2/2002 |
| WO | 2005025583 A2 | 3/2005 |
| WO | 2007069923 A1 | 6/2007 |
| WO | 2007093901 A1 | 8/2007 |
| WO | 2008011406 A2 | 1/2008 |
| WO | 2009091032 A1 | 7/2009 |
| WO | 2010077613 A1 | 7/2010 |
| WO | 2010133882 A1 | 11/2010 |
| WO | 2011031965 A1 | 3/2011 |
| WO | 2012080730 A1 | 6/2012 |

(Continued)

OTHER PUBLICATIONS

Diebold et al., "Innate Antiviral Responses by Means of TLR7-Mediated Recognition of Single-Stranded RNA," Science, 2004: 303, 1529-1531.
Lund et al., "Recognition of single-stranded RNA viruses by Toll-like receptor 7," PNAS, 2004: 101, 5598-5603.
Liu, Yong-Jun, "IPC: Professional Type 1 Interferon-Producing Cells and Plasmacytoid Dendritic Cell Precursors," Annu. Rev. Immunol., 2005: 23, 275-306.

(Continued)

*Primary Examiner* — Brenda L Coleman
(74) *Attorney, Agent, or Firm* — Ice Miller LLP

(57) ABSTRACT

A heteroaryl-pyrazole derivative, and a preparation method therefor and a medical application thereof are described. Specifically, a new heteroaryl-pyrazole derivative as shown in formula (I), a preparation method for the derivative, a pharmaceutical composition containing the derivative, and a use of the derivative as a therapeutic agent, in particular as a TLR7 agonist, are described. The substituents in formula (I) have the same definitions as in the description.

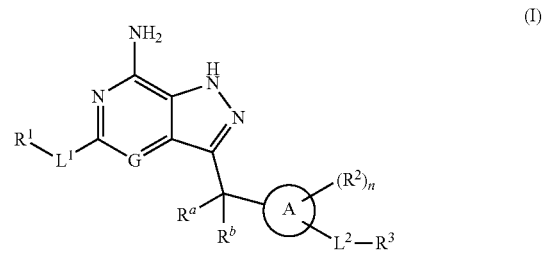

15 Claims, No Drawings

(56) References Cited

FOREIGN PATENT DOCUMENTS

WO    2013181579  A2    12/2013
WO    2016023511  A1    2/2016

OTHER PUBLICATIONS

Mahla et al., "Sweeten PAMPs: role of sugar complexed PAMPs in innate immunity and vaccine biology," Front Immunol. 4: 248 (2013).
International Search Report dated Aug. 30, 2018 in International Patent Application No. PCT/CN2018/087248 (with English translation).
Written Opinion dated Aug. 30, 2018 in International Patent Application No. PCT/CN2018/087248.
Extended European Search Report dated Nov. 6, 2020 in corresponding European Application No. 18803089.4.

HETEROARYL-PYRAZOLE DERIVATIVE, AND PREPARATION METHOD THEREFOR AND MEDICAL APPLICATION THEREOF

CROSS-REFERENCE TO RELATED APPLICATION

This application is a Section 371 of International Application No. PCT/CN2018/087248, filed May 17, 2018, which was published in the Chinese language on Nov. 22, 2018, under International Publication No. WO 2018/210298 A1, which claims priority under 35 U.S.C. § 119(b) to Chinese Patent Application No. 201710352719.5, filed on May 18, 2017, the disclosures of which are incorporated herein by reference in their entireties.

FIELD OF INVENTION

The present application belongs to medical field, relates to a new heteroaryl-pyrazole derivative as shown by general formula (I), a preparation method therefor, a pharmaceutical composition containing the derivative, and a use of the derivative as a therapeutic agent, in particular as a TLR7 agonist.

PRIOR ARTS

Toll-like receptors (TLRs) are a kind of important protein molecules involved in innate immunity. TLRs are non-catalytic receptors for monomer transmembrane, usually expressed in sentinel cells such as macrophages and dendritic cells, and can recognize structurally conserved molecules produced by microorganisms. Once these microorganisms break through physical barriers such as the skin or intestinal mucosa, they will be recognized by TLRs, which in turn activate immune cell responses (Mahla, R S. et al., Front Immunol. 4: 248 (2013)). The ability of the immune system to broadly recognize pathogenic microorganisms is partly due to the widespread presence of Toll-like immunoreceptors.

There are at least 10 different TLRs in mammals. Some ligands and corresponding signal cascade amplifications of these receptors have been identified. TLR7 is a member of TLRs (TLRs 3, 7, 8, and 9) subgroup, which is limited in the endosomal compartments of cells that specifically detect non-self nucleic acids. TLR7 plays a key role in recognizing ssRNA antiviral defense (Diebold S. S. et al, Science, 2004: 303, 1529-1531; and Lund J. M. et al, PNAS, 2004: 101, 5598-5603). TLR7 has a limited expression distribution in human and is expressed primarily by B cells and plasmacytoid dendritic cells (pDC), but to a less extent by monocytes. Plasmacytoid DCs are the only population of lymphoid-derived dendritic cells (0.2-0.8% of peripheral blood mononuclear cells (PBMCs)). They are the first type I interferon-producing cells that secrete high levels of interferon-α (IFNα) and interferon-β (IFNβ) in response to viral infections (Liu Y J, Annu. Rev. Immunol., 2005: 23, 275-306).

Many diseases and disorders are associated with abnormalities in TLRs such as melanoma, non-small cell lung cancer, hepatocellular carcinoma, basal cell carcinoma, renal cell carcinoma, myeloma, allergic rhinitis, asthma, chronic obstructive pneumonia disease (COPD), ulcerative colitis, liver fibrosis, HBV, Flaviviridae virus, HCV, HPV, RSV, SARS, HIV or influenza virus infection. Therefore, the use of TLRs agonists in treatment of related diseases is very promising.

Since TLR7 and TLR8 are highly homologous, TLR7 ligands are also TLR8 ligands in most cases. TLR8 stimulation mainly induces the production of cytokines such as tumor necrosis factor α (TNF-α) and chemokines. Interferon α is one of the main drugs for the treatment of chronic hepatitis B or hepatitis C, while TNF-α is a pro-inflammatory cytokine of which excessive secretion can cause serious side effects. Therefore, the selectivity of TLR7 and TLR8 is critical for the development of TLR7 agonists for the treatment of viral infectious diseases.

There have been currently related TLR7 agonist patent applications so far, such as WO2005025583, WO2007093901, WO2008011406, WO2009091032, WO2010077613, WO2010133882, WO2011031965, WO2012080730 and WO2016023511. Among them, WO2016023511 discloses a series of pyrrolopyrimidine compounds, such as embodiment 21

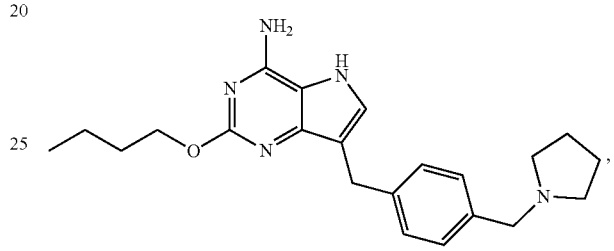

but the safety-related CYP and hERG data are not provided in this patent application. Safety and efficacy are important factors that must be paid attention to in drug research and development, and based on this, it is necessary to further explore and develop more effective and safer TLR7 agonists.

In the present application, it is found that the agonistic effect on TLR7 is significantly improved after the pyrrole ring in the pyrrolopyrimidine scaffold compounds of WO2016023511 is replaced by the pyrazole ring, and the inhibition on CYP and hERG thereof is also unexpectedly improved. Thus, the present application provides a TLR7 agonist with more potent activation effect on TLR7 activation, higher selectivity, better safety and more efficacy.

CONTENT OF THE PRESENT INVENTION

The present application is aimed to provide a compound as shown by general formula (I):

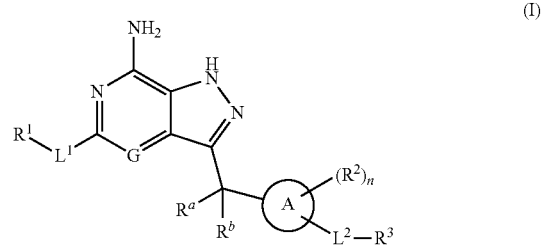

or a tautomer, a mesomer, a racemate, an enantiomer, a diastereomer thereof, or a mixture thereof, or a pharmaceutically acceptable salt thereof, wherein, ring A is selected from cycloalkyl, aryl and heteroaryl;

G is selected from N and $CR^4$;

L¹ is selected from —NR⁵—, —O—, —C(O)—, —S(O)ₘ—, —N(R⁵)C(O)—, —C(O)N(R⁵)—, —N(R⁵)S(O)₂—, —S(O)₂N(R⁵)— and a covalent bond;

R¹ is selected from hydrogen atom, alkyl, haloalkyl, alkenyl, alkynyl, cycloalkyl, heterocyclyl, aryl and heteroaryl, wherein, each of the alkyl, alkenyl, alkynyl, cycloalkyl, heterocyclyl, aryl and heteroaryl is independently and optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl and heteroaryl;

each R² is identical or different, and each is independently selected from hydrogen atom, halogen, alkyl, alkoxy, haloalkyl, hydroxy, hydroxyalkyl, cyano, amino, nitro, cycloalkyl, heterocyclyl, aryl, heteroaryl, —C(O)R⁶, —C(O)OR⁶, —S(O)ₘR⁶, —NR⁷R⁸ and —C(O)NR⁷R⁸, wherein, each of the alkyl, cycloalkyl, heterocyclyl, aryl and heteroaryl is independently and optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl and heteroaryl;

L² is selected from alkylene or a covalent bond, wherein, the alkylene is optionally substituted by one or more substituents selected from the group consisting of halogen, alkyl, alkoxy, haloalkyl, hydroxy, hydroxyalkyl, cyano, amino, nitro, cycloalkyl and heterocyclyl;

R³ is selected from hydrogen atom, alkyl, alkoxy, halogen, haloalkyl, hydroxy, hydroxyalkyl, cyano, amino, nitro, cycloalkyl, heterocyclyl, aryl, heteroaryl, —C(O)R⁶, —C(O)OR⁶, —S(O)ₘR⁶, —NR⁷R⁸ and —C(O)NR⁷R⁸, wherein, each of the cycloalkyl, heterocyclyl, aryl and heteroaryl is independently and optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —C(O)R⁶, —C(O)OR⁶, —S(O)ₘR⁶, —NR⁷R⁸ and —C(O)NR⁷R⁸;

Rᵃ and Rᵇ are identical or different, and each is independently selected from hydrogen atom, halogen, alkyl, alkoxy, haloalkyl, hydroxy, hydroxyalkyl, cyano, amino, nitro, cycloalkyl, heterocyclyl, aryl and heteroaryl;

R⁴ is selected from hydrogen atom, halogen, alkyl, alkoxy, haloalkyl, hydroxy, hydroxyalkyl, cyano, amino, nitro, cycloalkyl, heterocyclyl, aryl and heteroaryl;

R⁵ is selected from hydrogen atom, alkyl, haloalkyl, cycloalkyl, heterocyclyl, aryl and heteroaryl;

R⁶ is selected from hydrogen atom, alkyl, haloalkyl, amino, hydroxy, hydroxyalkyl, cycloalkyl, heterocyclyl, aryl and heteroaryl;

R⁷ and R⁸ are identical or different, and each is independently selected from hydrogen atom, alkyl, haloalkyl, cycloalkyl, heterocyclyl, aryl and heteroaryl, wherein, each of the alkyl, cycloalkyl, heterocyclyl, aryl and heteroaryl is independently and optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

or, R⁷ and R⁸ are linked together with the attached nitrogen atom to form heterocyclyl, wherein, except the one nitrogen atom, the heterocyclyl contains 1-2 identical or different heteroatoms selected from N, O and S, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

n is 0, 1, 2, 3 or 4; and
m is 0, 1 or 2.

In a preferred embodiment of the present application, the compound as shown by general formula (I) is a compound as shown by general formula (II):

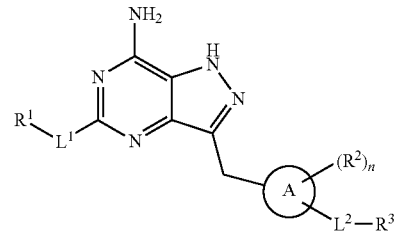

(II)

or a tautomer, a mesomer, a racemate, an enantiomer, a diastereomer thereof, or a mixture thereof, or a pharmaceutically acceptable salt thereof,
wherein,
the ring A, L¹-L², R¹-R³ and n are as defined in general formula (I).

In a preferred embodiment of the present application, the compound as shown by general formula (I), wherein the ring A is selected from phenyl and pyridyl.

In a preferred embodiment of the present application, the compound as shown by general formula (I) is a compound as shown by general formula (III):

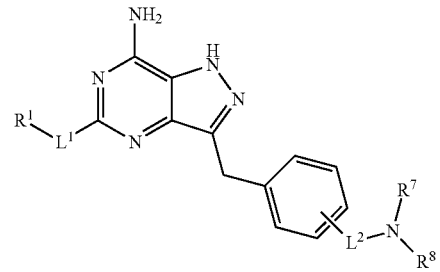

(III)

or a tautomer, a mesomer, a racemate, an enantiomer, a diastereomer thereof, or a mixture thereof, or a pharmaceutically acceptable salt thereof,
wherein,
R⁷ and R⁸ are linked together with the attached nitrogen atom to form heterocyclyl, wherein, besides the one nitrogen atom, the heterocyclyl contains 1-2 identical or different heteroatoms selected from N, O and S, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

L¹-L² and R¹ are as defined in general formula (I).

In a preferred embodiment of the present application, the compound as shown in general formula (I), wherein, L¹ is —O—.

In a preferred embodiment of the present application, the compound as shown in general formula (I), wherein, R¹ is alkyl.

In a preferred embodiment of the present application, the compound as shown in general formula (I), wherein, L² is alkylene.

Typical compounds of the present application include, but are not limited to:

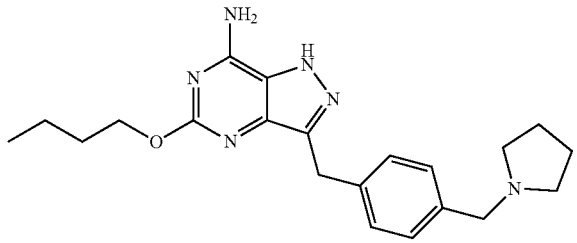

or a tautomer, a mesomer, a racemate, an enantiomer, a diastereomer thereof, or a mixture thereof, or a pharmaceutically acceptable salt thereof.

In a preferred embodiment of the present application, a compound as shown by general formula (IA), is an intermediate for preparing the compound as shown by general formula (I):

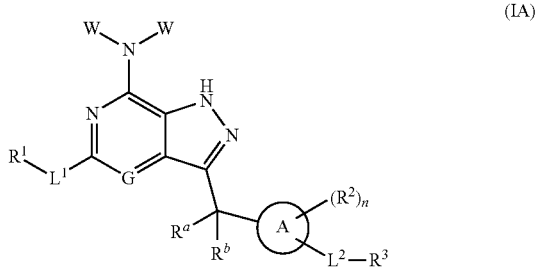

(IA)

or a tautomer, a mesomer, a racemate, an enantiomer, a diastereomer thereof, or a mixture thereof, or a pharmaceutically acceptable salt thereof, wherein, W is amino protecting group;

the ring A, G, $L^1$-$L^2$, $R^1$-$R^3$, $R^a$, $R^b$ and n are as defined in general formula (I).

The compound as shown by general formula (IA) includes, but is not limited to:

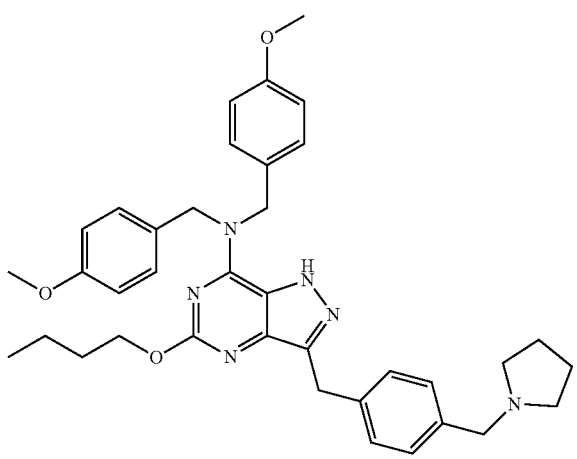

1j

Another aspect of the present application relates to a method for preparing the compound as shown by general formula (IA), comprising:

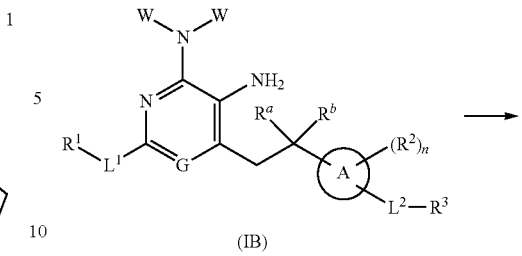

(IB)

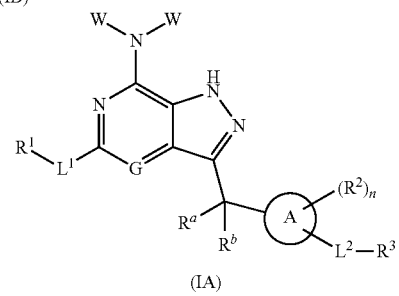

(IA)

carrying out a ring-closing reaction on a compound as shown by general formula (IB) and nitrite salt to give the compound as shown by general formula (IA);

wherein,

W is amino protecting group;

ring A, G, $L^1$-$L^2$, $R^1$-$R^3$, $R^a$, $R^b$ and n are as defined in general formula (IA).

Another aspect of the present application relates to a method for preparing the compound as shown by general formula (I), comprising:

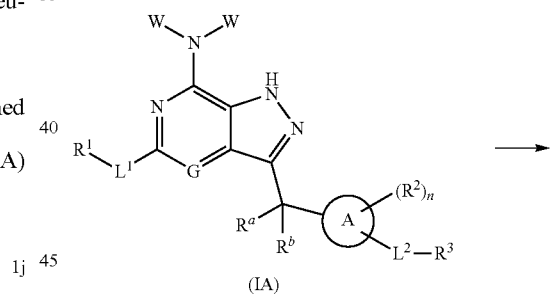

(IA)

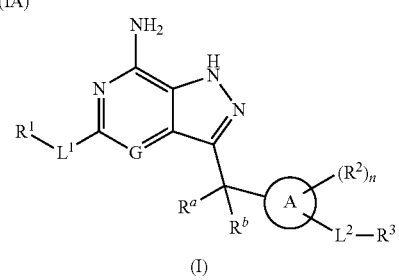

(I)

carrying out a de-protecting group reaction on the compound as shown by general formula (IA) to give the compound as shown by general formula (I);

wherein,

W is amino protecting group;

the ring A, G, $L^1$-$L^2$, $R^1$-$R^3$, $R^a$, $R^b$ and n are as defined in general formula (I).

In order to achieve the object of the present application, the following technical solutions are employed:

Solution 1

A method for preparing the compound as shown by general formula (I) or a tautomer, a mesomer, a racemate, an enantiomer, a diastereomer thereof, or a mixture thereof, or a pharmaceutically acceptable salt thereof of the present application, comprising the following steps of:

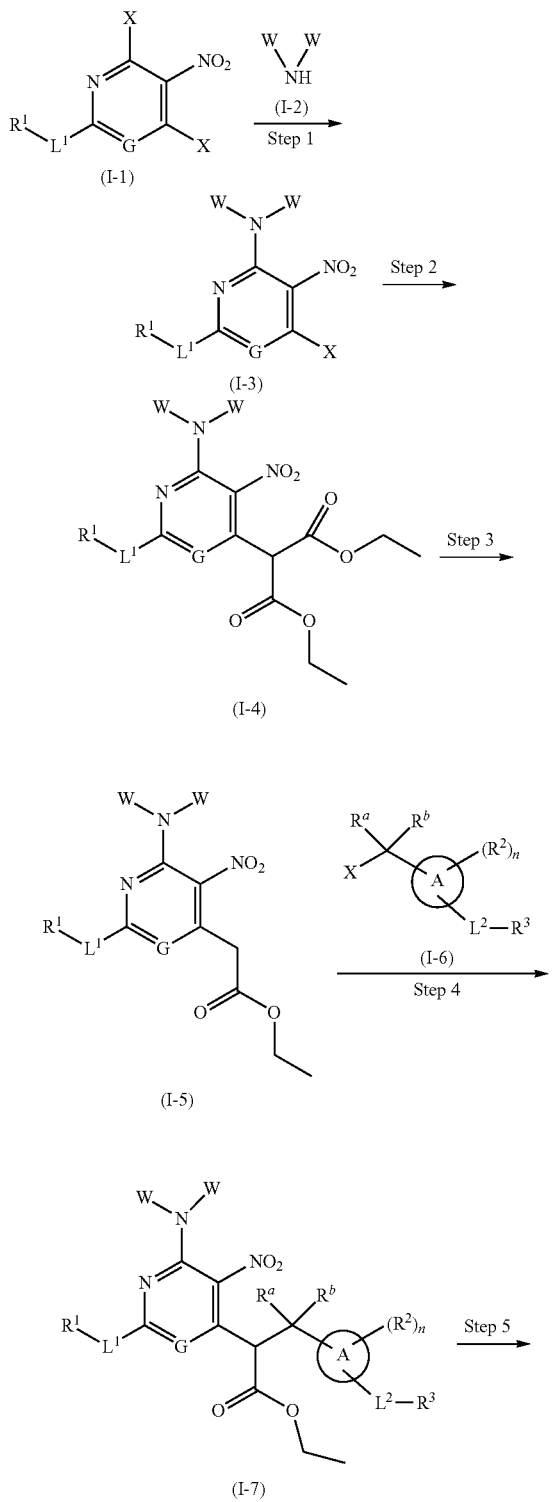

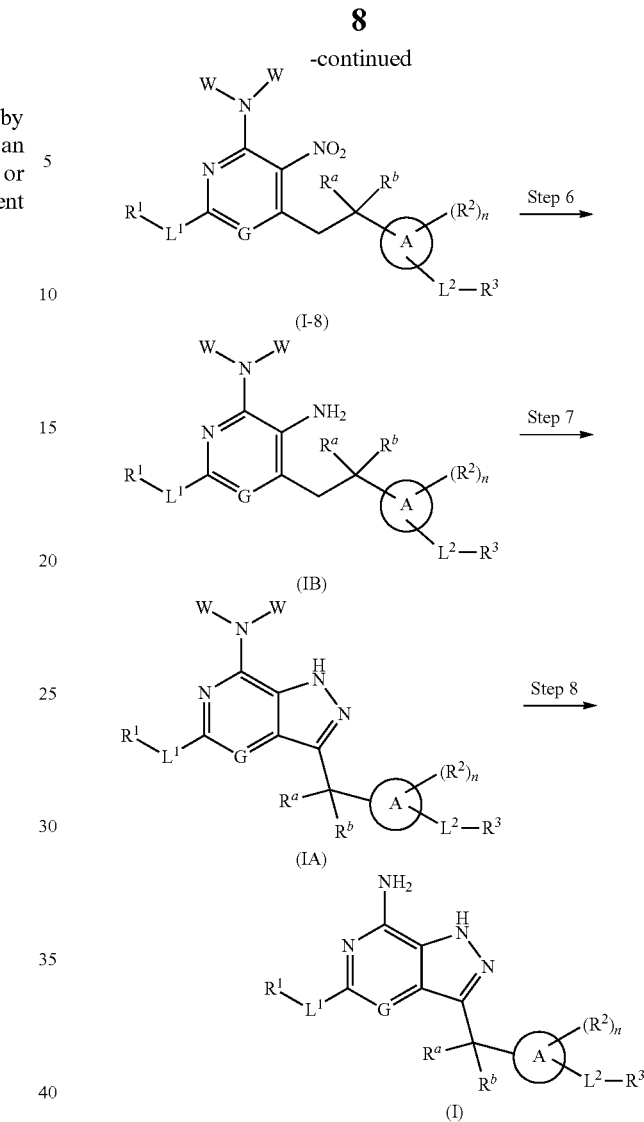

step 1, carrying out a nucleophilic substitution reaction on a compound as shown by general formula (I-1) and a compound as shown by general formula (I-2) under alkaline condition to give a compound as shown by general formula (I-3);

step 2, carrying out a nucleophilic substitution reaction on the compound as shown by general formula (I-3) and diethyl malonate under alkaline condition to give a compound as shown by general formula (I-4);

step 3, carrying out a hydrolyzation and decarboxylation reaction on the compound as shown by general formula (I-4) at high temperature in the presence of sodium chloride and DMSO to give a compound as shown by general formula (I-5);

step 4, carrying out a nucleophilic substitution reaction on the compound as shown by general formula (I-5) and a compound as shown by general formula (I-6) under alkaline condition to give a compound as shown by general formula (I-7);

step 5, carrying out a hydrolyzation and decarboxylation reaction on the compound as shown by general formula (I-7) under alkaline condition to give a compound as shown by general formula (I-8);

step 6, carrying out a reduction reaction on the compound as shown by general formula (I-8) in the presence of a reductant to give the compound as shown by general formula (IB);

step 7, reacting the compound as shown by general formula (I-B) with sodium nitrite under acidic condition to give the compound as shown by general formula (IA);

step 8, carrying out a de-protecting group reaction on the compound as shown by general formula (IA) under acidic condition to give the compound as shown by general formula (I);

wherein, the reagent that offers an alkaline condition includes organic bases and inorganic bases. The organic bases include, but are not limited to, triethylamine, pyridine, 4-dimethylaminopyridine, N,N-diisopropylethylamine, n-butyllithium, lithium diisopropylamide, lithium bis(trimethylsilyl)amine, potassium acetate, sodium tert-butoxide, potassium tert-butoxide and sodium n-butoxide. The inorganic bases include, but are not limited to, sodium hydride, potassium phosphate, sodium carbonate, potassium carbonate, potassium acetate, cesium carbonate, sodium hydroxide and lithium hydroxide;

the reagent that offers an acidic condition includes, but is not limited to, hydrogen chloride, hydrogen chloride in 1,4-dioxane solution, trifluoroacetic acid, formic acid, acetic acid, hydrochloric acid, sulfuric acid, methanesulfonic acid, nitric acid, phosphoric acid, p-toluenesulfonic acid, $Me_3SiCl$ and TMSOTf;

the reductant includes, but is not limited to, iron powder, zinc powder, lithium aluminum hydride, sodium borohydride, DIBAL-H, $NaAlH(O-t-Bu)_3$, $AlH_3$, $NaCNBH_3$, $Na(AcO)_3BH$, $B_2H_5$, $Li(Et)_3BH$, $Pd/C/H_2$ and (Raney Ni)/$H_2$;

the above reactions are preferably carried out in a solvent, and the solvent used includes, but is not limited to, acetic acid, trifluoroacetic acid, methanol, ethanol, n-butanol, toluene, tetrahydrofuran, dichloromethane, petroleum ether, ethyl acetate, n-hexane, dimethyl sulfoxide, 1,4-dioxane, water, N, N-dimethylformamide and a mixture thereof;

W is amino protecting group, preferably p-methoxybenzyl, tert-butoxycarbonyl, acetyl, benzyl and allyl;

X is halogen, preferably chlorine;

the ring A, G, $L^1$-$L^2$, $R^1$-$R^3$, $R^a$, $R^b$ and n are as defined in general formula (I).

Solution 2

A method for preparing the compound as shown by general formula (II) or a tautomer, a mesomer, a racemate, an enantiomer, a diastereomer thereof, or a mixture thereof, or a pharmaceutically acceptable salt thereof of the present application, comprising the following steps of:

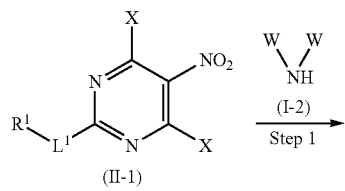

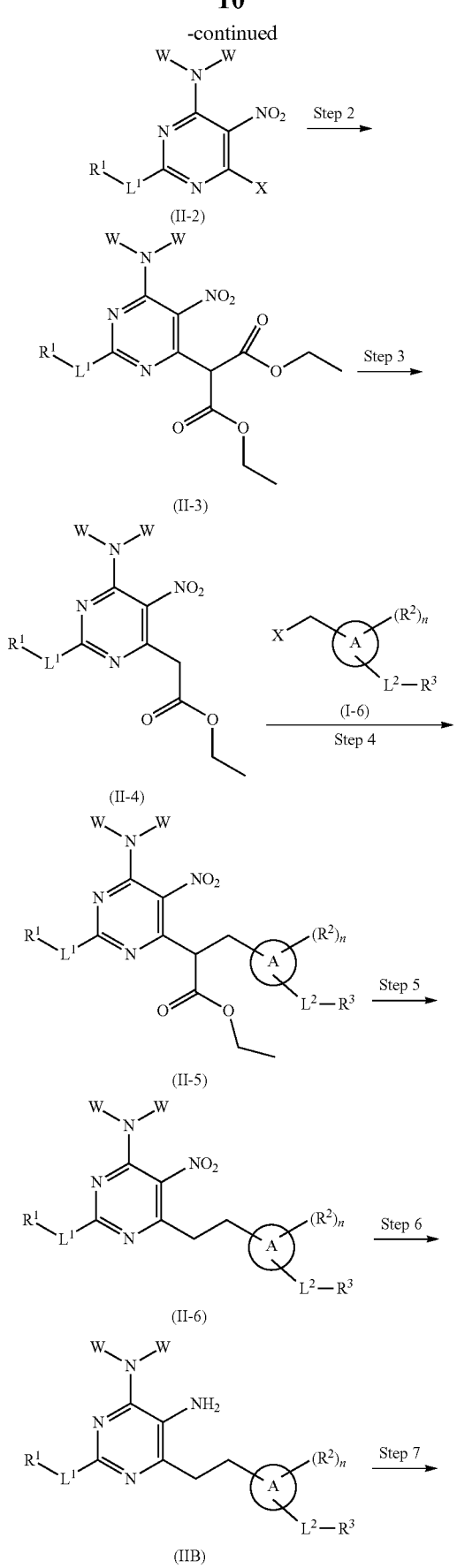

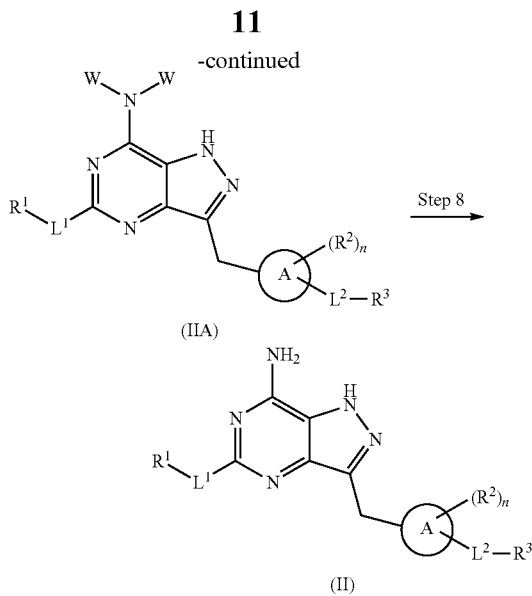

(IIA)

(II)

step 1, carrying out a nucleophilic substitution reaction on a compound as shown by general formula (II-1) and a compound as shown by general formula (I-2) under alkaline condition to give a compound as shown by general formula (II-2);

step 2, carrying out a nucleophilic substitution reaction on the compound as shown by general formula (II-2) and diethyl malonate under alkaline condition to give a compound as shown by general formula (II-3);

step 3, carrying out a hydrolyzation and decarboxylation reaction on the compound as shown by general formula (II-3) at high temperature in the presence of sodium chloride and DMSO to give a compound as shown by general formula (II-4);

step 4, carrying out a nucleophilic substitution reaction on the compound as shown by general formula (II-4) and a compound as shown by general formula (I-6) under alkaline condition to give a compound as shown by general formula (II-5);

step 5, carrying out a hydrolyzation and decarboxylation reaction on the compound as shown by general formula (II-5) under alkaline condition to give a compound as shown by general formula (II-6);

step 6, carrying out a reduction reaction on the compound as shown by general formula (II-6) in the presence of a reductant to give a compound as shown by general formula (IIB);

step 7, reacting the compound as shown by general formula (IIB) with sodium nitrite under acidic condition to give the compound as shown by general formula (IIA);

step 8, carrying out a de-protecting group reaction on the compound as shown by general formula (IIA) under acidic condition to give the compound as shown by general formula (I);

wherein, the reagent that offers an alkaline condition includes organic bases and inorganic bases. The organic bases include, but are not limited to, triethylamine, pyridine, 4-dimethylaminopyridine, N,N-diisopropylethylamine, n-butyllithium, lithium diisopropylamide, lithium bis(trimethylsilyl)amine, potassium acetate, sodium tert-butoxide, potassium tert-butoxide and sodium n-butoxide. The inorganic bases include, but are not limited to, sodium hydride, potassium phosphate, sodium carbonate, potassium carbonate, potassium acetate, cesium carbonate, sodium hydroxide and lithium hydroxide;

the reagent that offers an acidic condition includes, but is not limited to, hydrogen chloride, hydrogen chloride in 1,4-dioxane solution, trifluoroacetic acid, formic acid, acetic acid, hydrochloric acid, sulfuric acid, methanesulfonic acid, nitric acid, phosphoric acid, p-toluenesulfonic acid, Me$_3$SiCl and TMSOTf;

the reductant includes, but is not limited to, iron powder, zinc powder, lithium aluminum hydride, sodium borohydride, DIBAL-H, NaAlH(O-t-Bu)$_3$, AlH$_3$, NaCNBH$_3$, Na(AcO)$_3$BH, B$_2$H$_5$, Li(Et)$_3$BH, Pd/C/H$_2$ and (Raney Ni)/H$_2$;

the above reactions are preferably carried out in a solvent, and the solvent used includes, but is not limited to, acetic acid, trifluoroacetic acid, methanol, ethanol, n-butanol, toluene, tetrahydrofuran, dichloromethane, petroleum ether, ethyl acetate, n-hexane, dimethyl sulfoxide, 1,4-dioxane, water, N,N-dimethylformamide and a mixture thereof;

W is amino protecting group, preferably p-methoxybenzyl, tert-butoxycarbonyl, acetyl, benzyl and allyl;

X is halogen, preferably chlorine;

the ring A, $L^1$-$L^2$, $R^1$-$R^3$ and n are as defined in general formula (II).

Solution 3

A method for preparing the compound as shown by general formula (II) or a tautomer, a mesomer, a racemate, an enantiomer, a diastereomer thereof, or a mixture thereof, or a pharmaceutically acceptable salt thereof of the present application, comprising the following steps of:

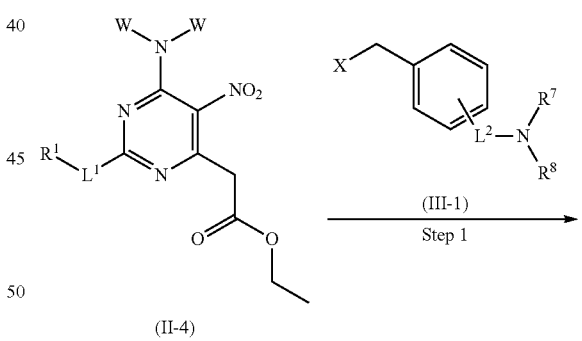

(II-4)

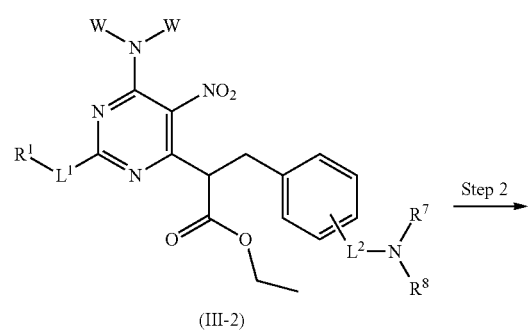

(III-2)

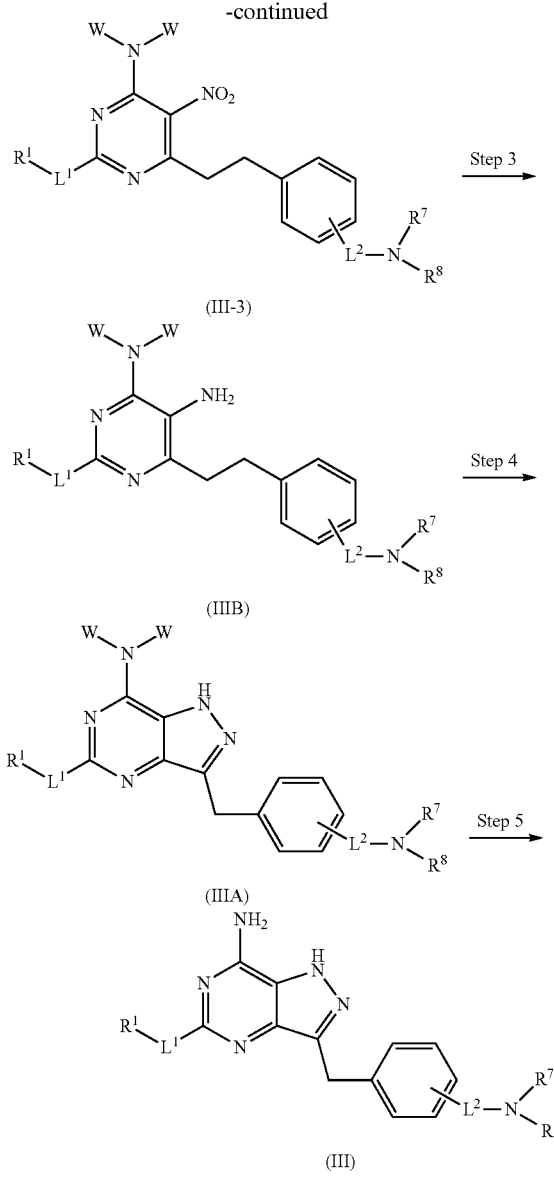

step 1, carrying out a nucleophilic substitution reaction on the compound as shown by general formula (II-4) and a compound as shown by general formula (III-1) under alkaline condition to give a compound as shown by general formula (III-2);

step 2, carrying out a hydrolyzation and decarboxylation reaction on the compound as shown by general formula (III-2) under alkaline condition to give a compound as shown by general formula (III-3);

step 3, carrying out a reduction reaction on the compound as shown by general formula (III-3) in the presence of a reductant to give a compound as shown by general formula (IIIB);

step 4, reacting the compound as shown by general formula (IIIB) with sodium nitrite under acidic condition to give a compound as shown by general formula (IIIA);

step 5, carrying out a de-protecting group reaction on the compound as shown by general formula (IIIA) under acidic condition to give a compound as shown by general formula (III);

wherein, the reagent that offers an alkaline condition includes organic bases and inorganic bases. The organic bases include, but are not limited to, triethylamine, pyridine, 4-dimethylaminopyridine, N,N-diisopropylethylamine, n-butyllithium, lithium diisopropylamide, lithium bis(trimethylsilyl)amine, potassium acetate, sodium tert-butoxide, potassium tert-butoxide and sodium n-butoxide. The inorganic bases include, but are not limited to, sodium hydride, potassium phosphate, sodium carbonate, potassium carbonate, potassium acetate, cesium carbonate, sodium hydroxide and lithium hydroxide;

the reagent that offers an acidic condition includes, but is not limited to, hydrogen chloride, hydrogen chloride in 1,4-dioxane solution, trifluoroacetic acid, formic acid, acetic acid, hydrochloric acid, sulfuric acid, methanesulfonic acid, nitric acid, phosphoric acid, p-toluenesulfonic acid, $Me_3SiCl$ and TMSOTf;

the reductant includes, but is not limited to, iron powder, zinc powder, lithium aluminum hydride, sodium borohydride, DIBAL-H, $NaAlH(O\text{-}t\text{-}Bu)_3$, $AlH_3$, $NaCNBH_3$, $Na(AcO)_3BH$, $B_2H_5$, $Li(Et)_3BH$, $Pd/C/H_2$ and (Raney Ni)/$H_2$;

the above reactions are preferably carried out in a solvent, and the solvent used includes, but is not limited to, acetic acid, trifluoroacetic acid, methanol, ethanol, n-butanol, toluene, tetrahydrofuran, dichloromethane, petroleum ether, ethyl acetate, n-hexane, dimethyl sulfoxide, 1,4-dioxane, water, N,N-dimethylformamide and a mixture thereof;

W is amino protecting group, preferably p-methoxybenzyl, tert-butoxycarbonyl, acetyl, benzyl and allyl;

X is halogen, preferably chlorine;

$L^1$-$L^2$, $R^1$ and $R^7$-$R^8$ are as defined in general formula (III).

In another aspect, the present application relates to a pharmaceutical composition comprising a therapeutically effective amount of the compound as shown by general formula (I), or the tautomer, the mesomer, the racemate, the enantiomer, the diastereomer thereof, or the mixture thereof, or the pharmaceutically acceptable salt thereof, and one or more pharmaceutically acceptable carriers, diluents or excipients. The present application further relates to the compound as shown by general formula (I), or the tautomer, the mesomer, the racemate, the enantiomer, the diastereomer thereof, or the mixture thereof, or the pharmaceutically acceptable salt thereof, or a medicament comprising the same, for use as a medicament.

The present application further relates to a use of the compound as shown by general formula (I), or the tautomer, the mesomer, the racemate, the enantiomer, the diastereomer thereof, or the mixture thereof, or the pharmaceutically acceptable salt thereof, or the pharmaceutical composition comprising the same in manufacturing a medicament for a TLR7 agonist.

The present application further relates to a use of the compound as shown by general formula (I), or the tautomer, the mesomer, the racemate, the enantiomer, the diastereomer thereof, or the mixture thereof, or the pharmaceutically acceptable salt thereof, or the pharmaceutical composition comprising the same in manufacturing a medicament for treating an infection caused by viruses.

The present application further relates to a use of the compound as shown by general formula (I), or the tautomer, the mesomer, the racemate, the enantiomer, the diastereomer thereof, or the mixture thereof, or the pharmaceutically acceptable salt thereof, or the pharmaceutical composition comprising the same in manufacturing a medicament for treating or preventing a cancer.

The present application further relates to a method for agonizing TLR7, comprising a step of contacting the compound as shown by general formula (I), or the tautomer, the mesomer, the racemate, the enantiomer, the diastereomer thereof, or the mixture thereof, or the pharmaceutically acceptable salt thereof, or the pharmaceutical composition comprising the same with TLR7.

The present application further relates to a method for treating an infection caused by viruses, comprising: administering to a patient in need thereof a therapeutically effective amount of the compound as shown by general formula (I), or the tautomer, the mesomer, the racemate, the enantiomer, the diastereomer thereof, or the mixture thereof, or the pharmaceutically acceptable salt thereof, or the pharmaceutical composition comprising the same.

The present application further relates to a method for treating or preventing a cancer, comprising: administering to a patient in need thereof a therapeutically effective amount of the compound as shown by general formula (I), or the tautomer, the mesomer, the racemate, the enantiomer, the diastereomer thereof, or the mixture thereof, or the pharmaceutically acceptable salt thereof, or the pharmaceutical composition comprising the same.

The present application further relates to the compound as shown by general formula (I), or the tautomer, the mesomer, the racemate, the enantiomer, the diastereomer thereof, or the mixture thereof, or the pharmaceutically acceptable salt thereof, or the pharmaceutical composition comprising the same, for use as a TLR7 agonist.

The present application further relates to the compound as shown by general formula (I), or the tautomer, the mesomer, the racemate, the enantiomer, the diastereomer thereof, or the mixture thereof, or the pharmaceutically acceptable salt thereof, or the pharmaceutical composition comprising the same, for use in treating or preventing an infection caused by viruses.

The present application further relates to the compound as shown by general formula (I), or the tautomer, the mesomer, the racemate, the enantiomer, the diastereomer thereof, or the mixture thereof, or the pharmaceutically acceptable salt thereof, or the pharmaceutical composition comprising the same, for use in treating or preventing a cancer.

In the present application, the virus is preferably selected from dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, Zika virus, HIV, HBV, HCV, HPV, RSV, SARS and influenza virus, more preferably selected from HBV and HCV.

In the present application, the cancer is preferably selected from melanoma, non-small cell lung cancer, hepatocellular carcinoma, basal cell carcinoma, renal cell carcinoma or myeloma. The pharmaceutical composition containing the active ingredient can be in a form suitable for oral administration, for example, tablet, troche, lozenge, aqueous or oily suspension, dispersible powder or granule, emulsion, hard or soft capsule, or syrup or elixir. The oral composition can be prepared according to any known method in the art for the preparation of pharmaceutical composition, and such composition can contain one or more ingredients selected from sweeteners, flavoring agents, colorants and preservatives, in order to provide a pleasing and palatable pharmaceutical preparation. The tablet contains the active ingredient in admixture with nontoxic pharmaceutically acceptable excipients suitable for the tablets manufacture.

The aqueous suspension contains the active ingredient in admixture with excipients suitable for an aqueous suspension manufacture. The aqueous suspension can also contain one or more preservatives, one or more colorants, one or more flavoring agents, and one or more sweeteners.

The oily suspension can be formulated by suspending the active ingredient in a vegetable oil. The oily suspension can contain a thickener. The aforementioned sweeteners and flavoring agents can be added to provide a palatable formulation.

The pharmaceutical composition of the present application can also be in the form of an oil-in-water emulsion.

The pharmaceutical composition can be in the form of a sterile injectable aqueous solution. Acceptable vehicles or solvents that can be used are water, Ringer's solution and isotonic sodium chloride solution. The sterile injectable formulation can be a sterile injectable oil-in-water microemulsion in which the active ingredient is dissolved in the oil phase. For example, the active ingredient is dissolved in a mixture of soybean oil and lecithin. The oil solution is then added to a mixture of water and glycerin to form a microemulsion. The injectable solution or micro-emulsion can be introduced into a patient's bloodstream by local bolus injection. Alternatively, the solution and micro-emulsion are preferably administered in a manner that maintains a constant circulating concentration of the compound of the present application. In order to maintain this constant concentration, a continuous intravenous delivery device can be used. An example of such a device is Deltec CADD-PLUS™ 5400 intravenous pump.

The pharmaceutical composition of the present application can be in the form of a sterile injectable aqueous or oily suspension for intramuscular and subcutaneous administration. Such a suspension can be formulated with suitable dispersants or wetting agents and suspending agents as described above according to known techniques. The sterile injectable formulation can also be a sterile injectable solution or suspension prepared in a nontoxic parenterally acceptable diluent or solvent. Moreover, sterile fixed oils can easily be used as a solvent or suspending medium.

The compound of the present application can be administered in the form of a suppository for rectal administration. These pharmaceutical compositions can be prepared by mixing the drug with a suitable non-irritating excipient that is a solid at ordinary temperatures, but a liquid in the rectum, thereby melting in the rectum to release the drug. Such materials include cocoa butter, glycerin gelatin, hydrogenated vegetable oil, a mixture of polyethylene glycols of various molecular weights and fatty acid esters thereof.

It is well known to those skilled in the art that the dosage of a drug depends on a variety of factors, including but not limited to, the following factors: activity of a specific compound, age of the patient, weight of the patient, general health of the patient, behavior of the patient, diet of the patient, administration time, administration route, excretion rate, drug combination and the like. In addition, the optimal treatment such as treatment mode, daily dose of the compound as shown by general formula (I) or the type of the pharmaceutically acceptable salt, can be verified by traditional therapeutic regimens.

Definition and Description

Unless opposite stated, the terms used in the specification and claims have the meanings described below.

The term "alkyl" refers to a saturated aliphatic hydrocarbon group, which is a straight or branched chain group comprising 1 to 20 carbon atoms, preferably an alkyl comprising 1 to 12 carbon atoms, and more preferably an alkyl comprising 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. Non-limiting examples of a lower alkyl comprising 1 to 6 carbon atoms, include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted, and when substituted, the substituent(s) can be substituted at any available connection site. The substituent is preferably one or more groups independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclyloxy, cycloalkylthio, heterocycloalkylthio, oxo, —C(O)R$^6$, —C(O)OR$^6$, —S(O)$_m$R$^6$, —NR$^7$R$^8$ and —C(O)NR$^7$R$^8$.

The term "alkylene" refers to a saturated straight or branched aliphatic hydrocarbon group comprising two residues derived from the removal of two hydrogen atoms from the same carbon atom of the parent alkane or two different carbon atoms, is a linear or branched group comprising 1 to 20 carbon atoms, preferably comprising 1 to 12 carbon atoms, more preferably an alkylene group comprising 1 to 6 carbon atoms. Non-limiting examples of alkylene groups include, but are not limited to, methylene (—CH$_2$—), 1,1-ethylene (—CH(CH$_3$)—), 1,2-ethylene (—CH$_2$CH$_2$—), 1,1-propylene (—CH(CH$_2$CH$_3$)—), 1,2-propylene (—CH$_2$CH(CH$_3$)—), 1,3-propylene (—CH$_2$CH$_2$CH$_2$—), 1,4-butylidene (—CH$_2$CH$_2$CH$_2$CH$_2$—), and the like. The alkylene group can be substituted or unsubstituted, and when substituted, the substituent(s) can be substituted at any available connection site, preferably one or more groups independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocycloalkylthio, oxo, —C(O)R$^6$, —C(O)OR$^6$, —S(O)$_m$R$^6$, —NR$^7$R$^8$ and —C(O)NR$^7$R$^8$.

The term "alkenyl" refers to an unsaturated alkyl containing a carbon-carbon double bond in the molecule, and the alkyl is as defined above. The alkenyl group can be substituted or unsubstituted, and when substituted, the substituent is preferably one or more groups independently selected from the following group consisting of hydrogen atom, alkyl, alkoxy, halogen, haloalkyl, hydroxyl, hydroxyalkyl, cyano, amino, nitro, cycloalkyl, heterocyclyl, aryl, heteroaryl, —C(O)R$^6$, —C(O)OR$^6$, —S(O)$_m$R$^6$, —NR$^7$R$^8$ and —C(O)NR$^7$R$^8$.

The term "alkynyl" refers to an unsaturated alkyl containing a carbon-carbon triple bond in the molecule, and the alkyl is as defined above. The alkynyl group can be substituted or unsubstituted, and when substituted, the substituent is preferably one or more groups independently selected from the following group consisting of hydrogen atom, alkyl, alkoxy, halogen, haloalkyl, hydroxyl, hydroxyalkyl, cyano, amino, nitro, cycloalkyl, heterocyclyl, aryl, heteroaryl, —C(O)R$^6$, —C(O)OR$^6$, —S(O)$_m$R$^6$, —NR$^7$R$^8$ and —C(O)NR$^7$R$^8$.

The term "cycloalkyl" refers to a saturated or partially unsaturated monocyclic or polycyclic hydrocarbon substituent group comprising 3 to 20 carbon atoms, preferably 3 to 12 carbon atoms, more preferably 3 to 6 carbon atoms, and most preferably 5 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl comprising a spiro ring, fused ring and bridged ring.

The term "spiro cycloalkyl" refers to a 5 to 20 membered polycyclic group with monocyclic rings connected through one shared carbon atom (called a spiro atom), and the rings can contain one or more double bonds, but none of the rings has a completely conjugated it-electron system, and the spiro cycloalkyl is preferably 6 to 14 membered spiro cycloalkyl, and more preferably 7 to 10 membered spiro cycloalkyl. According to the number of the spiro atoms shared between the rings, the spiro cycloalkyl can be divided into mono-spiro cycloalkyl, di-spiro cycloalkyl, or poly-spiro cycloalkyl, and preferably a mono-spiro cycloalkyl or di-spiro cycloalkyl, and more preferably 4-membered/4-membered, 4-membered/5-membered, 4-membered/6-membered, 5-membered/5-membered, or 5-membered/6-membered mono-spiro cycloalkyl. Non-limiting examples of spiro cycloalkyl include:

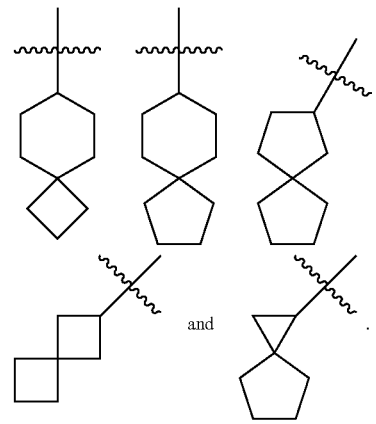

The term "fused cycloalkyl" refers to a 5 to 20 membered all-carbon polycyclic group, wherein each ring in the system shares an adjacent pair of carbon atoms with another ring, wherein one or more rings can contain one or more double bonds, but none of the rings has a completely conjugated it-electron system. The fused cycloalkyl is preferably 6 to 14 membered fused cycloalkyl, and more preferably 7 to 10 membered fused cycloalkyl. According to the number of membered rings, the fused cycloalkyl can be divided into bicyclic, tricyclic, tetracyclic or polycyclic fused cycloalkyl, and preferably bicyclic or tricyclic fused cycloalkyl, and more preferably 5-membered/5-membered, or 5-membered/ 6-membered bicyclic fused cycloalkyl. Non-limiting examples of fused cycloalkyl include:

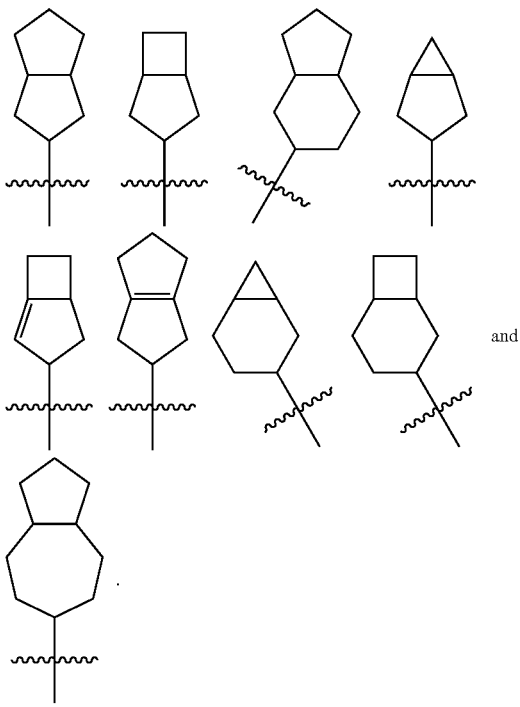

The term "bridged cycloalkyl" refers to a 5 to 20 membered all-carbon polycyclic group, wherein every two rings in the system share two disconnected carbon atoms, wherein the rings can have one or more double bonds, but none of the rings has a completely conjugated it-electron system. The bridged cycloalkyl is preferably 6 to 14 membered bridged cycloalkyl, and more preferably 7 to 10 membered bridged cycloalkyl. According to the number of membered rings, the bridged cycloalkyl can be divided into bicyclic, tricyclic, tetracyclic or polycyclic bridged cycloalkyl, and preferably bicyclic, tricyclic or tetracyclic bridged cycloalkyl, and more preferably bicyclic or tricyclic bridged cycloalkyl. Non-limiting examples of bridged cycloalkyls include:

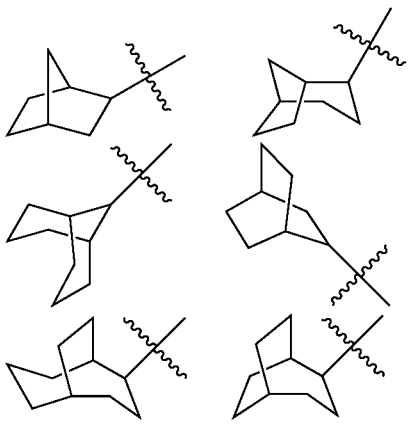

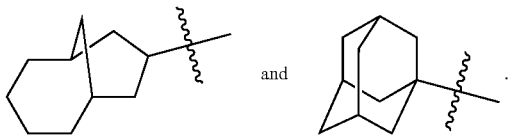

The ring of cycloalkyl can be fused to the ring of aryl, heteroaryl or heterocycloalkyl, wherein the ring bound to the parent structure is cycloalkyl. Non-limiting examples include indanyl, tetrahydronaphthyl, benzocycloheptyl and the like, and preferably benzocycloheptyl or tetrahydronaphthyl. The cycloalkyl can be optionally substituted or unsubstituted, and when substituted, the substituent(s) is preferably one or more following group(s) independently optionally selected from the group consisting of alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, heterocycloalkylthio, oxo, carboxy or carboxylate.

The term "heterocyclyl" refers to a 3 to 20 membered saturated or partially unsaturated monocyclic or polycyclic hydrocarbon group, wherein one or more ring atoms are heteroatoms selected from the group consisting of N, O and $S(O)_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms; more preferably, the heterocyclyl has 3 to 8 ring atoms wherein 1 to 3 atoms are heteroatoms, and most preferably 5 to 6 ring atoms wherein 1 to 2 atoms or 1 to 3 atoms are heteroatoms. Non-limiting examples of monocyclic heterocyclyl include pyrrolidyl, imidazolidinyl, tetrahydrofuranyl, tetrahydropyranyl, tetrahydrothiophenyl, dihydroimidazolyl, dihydrofuranyl, dihydropyrazolyl, dihydropyrrolyl, piperidinyl, piperazinyl, morpholinyl, thiomorpholinyl, homopiperazinyl and the like, and preferably tetrahydrofuranyl, piperidinyl or pyrrolidyl. Polycyclic heterocyclyl includes heterocyclyl comprising a spiro ring, fused ring or bridged ring.

The term "spiro heterocyclyl" refers to a 5 to 20 membered polycyclic heterocyclyl group with monocyclic rings connected through one shared atom (called a spiro atom), wherein one or more ring atoms are heteroatoms selected from the group consisting of N, O and $S(O)_m$ (wherein m is an integer of 0 to 2), with the remaining ring atoms being carbon atoms, where the rings can contain one or more double bonds, but none of the rings has a completely conjugated π-electron system. The spiro heterocyclyl is preferably 6 to 14 membered spiro heterocyclyl, and more preferably 7 to 10 membered spiro heterocyclyl. According to the number of the spiro atoms shared between the rings, the spiro heterocyclyl can be divided into mono-spiro heterocyclyl, di-spiro heterocyclyl, or poly-spiro heterocyclyl, and is preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Non-limiting examples of spiro heterocyclyls include:

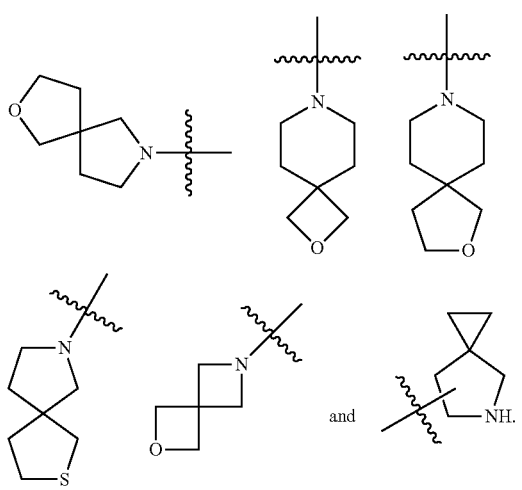
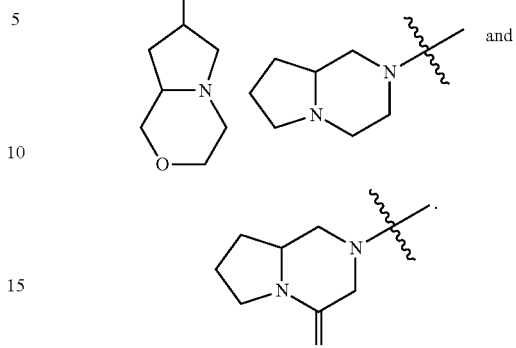

The term "fused heterocyclyl" refers to a 5 to 20 membered polycyclic heterocyclyl group, wherein each ring in the system shares an adjacent pair of atoms with another ring, where the one or more rings can contain one or more double bonds, but none of the rings has a completely conjugated π-electron system, wherein one or more ring atoms are heteroatoms selected from the group consisting of N, O and $S(O)_m$ (wherein m is an integer of 0 to 2), with the remaining ring atoms being carbon atoms. The fused heterocyclyl is preferably 6 to 14 membered fused heterocyclyl, and more preferably 7 to 10 membered fused heterocyclyl. According to the number of membered rings, the fused heterocyclyl can be divided into bicyclic, tricyclic, tetracyclic or polycyclic fused heterocyclyl, and the fused heterocyclyl is preferably bicyclic or tetracyclic fused heterocyclyl, and more preferably 5-membered/5-membered or 5-membered/6-membered bicyclic fused heterocyclyl. Non-limiting examples of fused heterocyclyl include:

The term "bridged heterocyclyl" refers to a 5 to 14 membered polycyclic heterocyclyl group, wherein every two rings in the system share two disconnected atoms, wherein the rings can have one or more double bonds, but none of the rings has a completely conjugated π-electron system, wherein one or more ring atoms are heteroatoms selected from the group consisting of N, O and $S(O)_m$ (wherein m is an integer of 0 to 2), with the remaining ring atoms being carbon atoms. The bridged heterocyclyl is preferably 6 to 14 membered bridged heterocyclyl, and more preferably 7 to 10 membered bridged heterocyclyl. According to the number of membered rings, the bridged heterocyclyl can be divided into bicyclic, tricyclic, tetracyclic or polycyclic bridged heterocyclyl, and the bridged heterocyclyl is preferably bicyclic, tricyclic or tetracyclic bridged heterocyclyl, and more preferably bicyclic or tricyclic bridged heterocyclyl. Non-limiting examples of bridged heterocyclyls include:

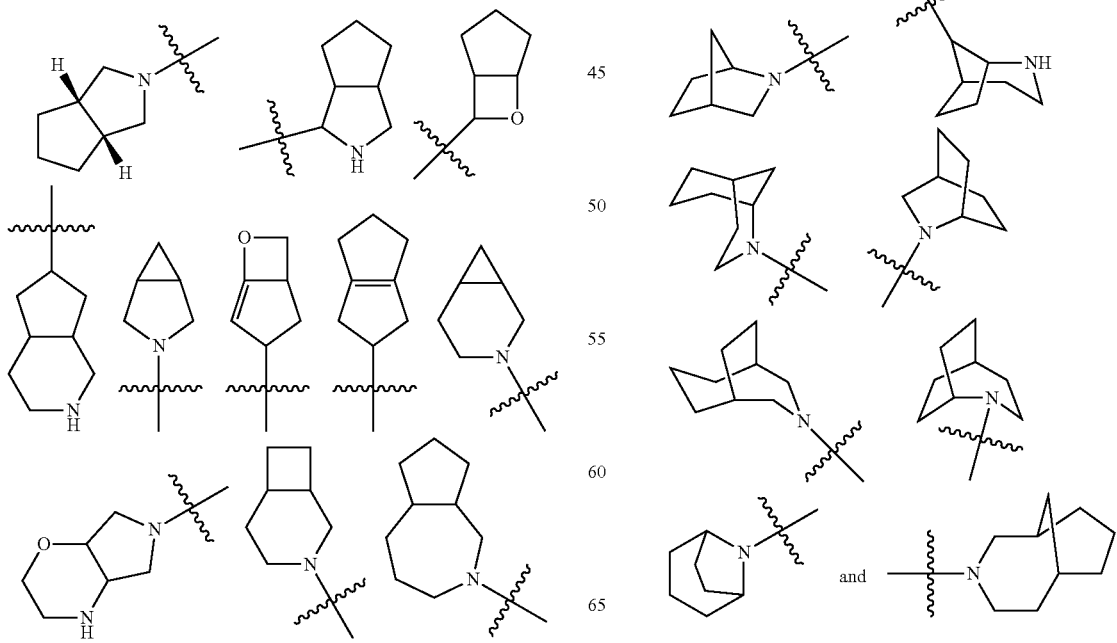

The ring of heterocyclyl can be fused to the ring of aryl, heteroaryl or cycloalkyl, wherein the ring bound to the parent structure is heterocyclyl. Non-limiting examples thereof include:

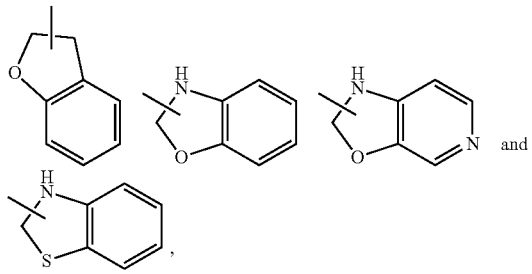

and the like.

The heterocyclyl can be optionally substituted or unsubstituted, and when substituted, the substituent(s) is preferably one or more group(s) independently optionally selected from the following group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, oxo, —C(O)R$^6$, —C(O)OR$^6$, —S(O)$_m$R$^6$, —NR$^7$R$^8$ and —C(O)NR$^7$R$^8$.

The term "aryl" refers to a 6 to 14 membered all-carbon monocyclic ring or polycyclic fused ring (that is, each ring in the system shares an adjacent pair of carbon atoms with another ring in the system) having a conjugated π-electron system, preferably 6 to 10 membered aryl, more preferably 5 to 6 membered aryl, for example, phenyl and naphthyl. The ring of aryl can be fused to the ring of heteroaryl, heterocyclyl or cycloalkyl, wherein the ring bound to the parent structure is aryl ring. Non-limiting examples thereof include:

The aryl can be substituted or unsubstituted, and when substituted, the substituent(s) is preferably one or more group(s) independently optionally selected from the following group consisting of alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, heterocycloalkylthio, —C(O)R$^6$, —C(O)OR$^6$, —S(O)$_m$R$^6$, —NR$^7$R$^8$ and —C(O)NR$^7$R$^8$.

The term "amino protecting group" is intended to keep the amino group unchanged during the reaction of other parts of the molecule, and to protect the amino group with a group which is easily to remove. Non-limiting examples include t-butoxycarbonyl, acetyl, benzyl, allyl, p-methoxybenzyl, and the like. These groups can be optionally substituted by 1 to 3 substituents selected from the group consisting of halogen, alkoxy and nitro. The amino protecting group is preferably p-methoxybenzyl.

The term "heteroaryl" refers to a 5 to 14 membered heteroaromatic system comprising 1 to 4 heteroatoms selected from the group consisting of O, S and N. The heteroaryl is preferably 5 to 10 membered heteroaryl comprising 1 to 3 heteroatoms, more preferably 5 or 6 membered heteroaryl comprising 1 to 2 heteroatoms, preferably for example, imidazolyl, furyl, thienyl, thiazolyl, pyrazolyl, oxazolyl, pyrrolyl, tetrazolyl, pyridyl, pyrimidinyl, thiadiazole, pyrazinyl and the like, preferably imidazolyl, pyrazolyl, or pyrimidinyl, thiazolyl; more preferably pyrazolyl. The ring of heteroaryl can be fused to the ring of aryl, heterocyclyl or cycloalkyl, wherein the ring bound to the parent structure is heteroaryl ring. Non-limiting examples thereof include:

The heteroaryl can be optionally substituted or unsubstituted, and when substituted, the substituent(s) is preferably one or more group(s) independently optionally selected from the following group consisting of alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, heterocycloalkylthio, —C(O)R$^6$, —C(O)OR$^6$, —S(O)$_m$R$^6$, —NR$^7$R$^8$ and —C(O)NR$^7$R$^8$.

The term "alkoxy" refers to an —O-(alkyl) or an —O-(unsubstituted cycloalkyl), wherein the alkyl and cycloalkyl are as defined above. Non-limiting examples of alkoxy include: methoxy, ethoxy, propoxy, butoxy, cyclopropyloxy, cyclobutyloxy, cyclopentyloxy, cyclohexyloxy. The alkoxy can be optionally substituted or unsubstituted, and when substituted, the substituent(s) is preferably one or more group(s) independently optionally selected from the following group consisting of hydrogen atom, halogen, alkyl, alkoxy, haloalkyl, hydroxy, hydroxyalkyl, cyano, amino, nitro, cycloalkyl, heterocyclyl, aryl and heteroaryl.

The term "haloalkyl" refers to alkyl substituted by one or more halogens, wherein the alkyl is as defined above. The term "hydroxy" refers to —OH group.

The term "hydroxyalkyl" refers to alkyl substituted by hydroxyl(s), wherein the alkyl is as defined above.

The term "halogen" refers to fluorine, chlorine, bromine or iodine.

The term "amino" refers to —NH$_2$.

The term "cyano" refers to —CN.

The term "nitro" refers to —NO$_2$.

The term "oxo" refers to =O.

"Optional" or "optionally" means that the event or circumstance described subsequently can, but not, occur, and such a description includes the situation in which the event or circumstance does or does not occur. For example, "the heterocyclyl optionally substituted by alkyl" means that alkyl group can be, but need not be present, and such a description includes the situation of the heterocyclyl being substituted by alkyl and the heterocyclyl being not substituted by alkyl.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical position, and the person skilled in the art is able to determine whether the substitution is possible or impossible (by experiments or theory) without paying excessive efforts. For example, the combination of amino or hydroxy having free hydrogen and carbon atoms comprising unsaturated bonds (such as olefinic) can be unstable.

"Pharmaceutical composition" refers to a mixture of one or more of the compounds according to the present application or physiologically/pharmaceutically acceptable salts or prodrugs thereof with other chemical components, and other components such as physiologically/pharmaceutically acceptable carriers and excipients. The purpose of the pharmaceutically composition is to facilitate administration of a compound to an organism, which is conducive to the absorption of the active ingredient so as to show biological activity.

"Pharmaceutical acceptable salt" refers to a salt of the compound of the present application, which is safe and effective in mammals and has the desired biological activity.

m and R$^6$-R$^8$ are as defined in general formula (I).

DETAILED DESCRIPTION OF THE PREFERRED EMBODIMENT

In the following embodiments, the structures of the compounds were identified by nuclear magnetic resonance (NMR) and/or mass spectrometry (MS). NMR shifts (δ) are given in 10$^{-6}$ (ppm). NMR was determined by a Bruker AVANCE-400 machine, the solvents for determination were deuterated-dimethyl sulfoxide (DMSO-d$_6$), deuterated-chloroform (CDCl$_3$) and deuterated-methanol (CD$_3$OD), and the internal standard was tetramethyl silane (TMS).

MS was determined by a FINNIGAN LCQAd (ESI) mass spectrometer (manufacturer: Thermo, type: Finnigan LCQ advantage MAX).

High performance liquid chromatography (HPLC) was performed on an Agilent 1200DAD high pressure liquid chromatograph (Sunfire C18 150×4.6 mm chromatographic column), and a Waters 2695-2996 high pressure liquid chromatography spectrometer (Gimini C18 150×4.6 mm chromatographic column).

Chiral HPLC was performed on a LC-10A vp (Shimadzu) or SFC-analytical (Berger Instruments Inc.);

Yantai Huanghai HSGF254 or Qingdao GF254 silica gel plate was used as the thin-layer silica gel chromatography (TLC) plate. The dimension of the silica gel plate used in TLC was 0.15 mm to 0.2 mm, and the dimension of the silica gel plate used in product purification was 0.4 mm to 0.5 mm.

Yantai Huanghai 200 to 300 mesh silica gel was generally used as a carrier for column chromatography.

Prep Star SD-1 (Varian Instruments Inc.) or SFC-multigram (Berger Instruments Inc.) was used for chiral preparative column chromatography.

The average kinase inhibition rates and IC$_{50}$ values were determined by a NovoStar ELISA (BMG Co., Germany).

The known starting materials of the present application can be prepared by the known methods in the art, or can be purchased from ABCR GmbH & Co. KG, Acros Organnics, Aldrich Chemical Company, Accela ChemBio Inc., or Dari chemical Company, etc.

Unless specially stated in embodiments, the reactions were carried out under argon atmosphere or nitrogen atmosphere.

Argon atmosphere or nitrogen atmosphere means that a reaction flask is equipped with an argon or nitrogen balloon (about 1 L).

Hydrogen atmosphere means that a reaction flask is equipped with a hydrogen balloon (about 1 L).

Pressurized hydrogenation reactions were performed on a Parr 3916EKX hydrogenation instrument and a Qinglan QL-500 hydrogen generator or HC2-SS hydrogenation instrument.

In hydrogenation reactions, the reaction system was generally vacuumed and filled with hydrogen, with the above operation was repeated three times.

CEM Discover-S 908860 type microwave reactor was used in microwave reactions.

Unless specially stated in embodiments, the solution refers to an aqueous solution.

Unless specially stated in embodiments, the reaction temperature is room temperature from 20° C. to 30° C.

The reaction processes in embodiments were monitored by thin layer chromatography (TLC). The developing solvent used in the reactions, the eluting system in column chromatography and the developing solvent system in thin layer chromatography for purification of the compounds included: A: n-hexane/ethyl acetate system, and the ratio of the volume of the solvent was adjusted according to the polarity of the compounds, and a small quantity of alkaline reagent such as triethylamine or acidic reagent such as acetic acid could also be added for adjustment.

Embodiment 1
5-Butoxy-3-(4-(pyrrolidin-1-ylmethyl)benzyl)-1H-pyrazolo[4,3-d]pyrimidin-7-amine 1
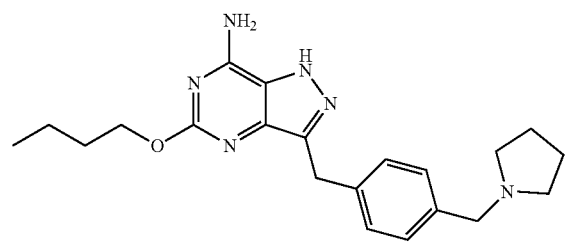
1
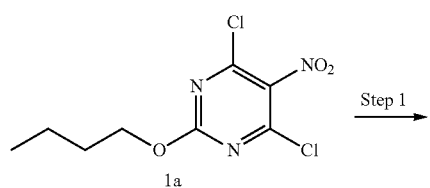
1a → Step 1
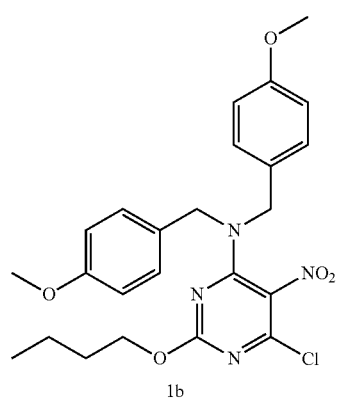
1b → Step 2
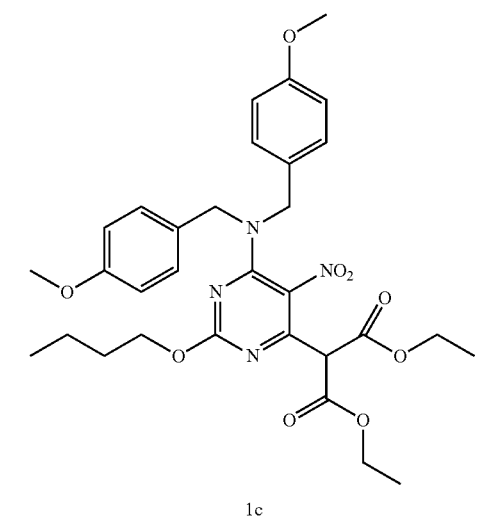
1c → Step 3
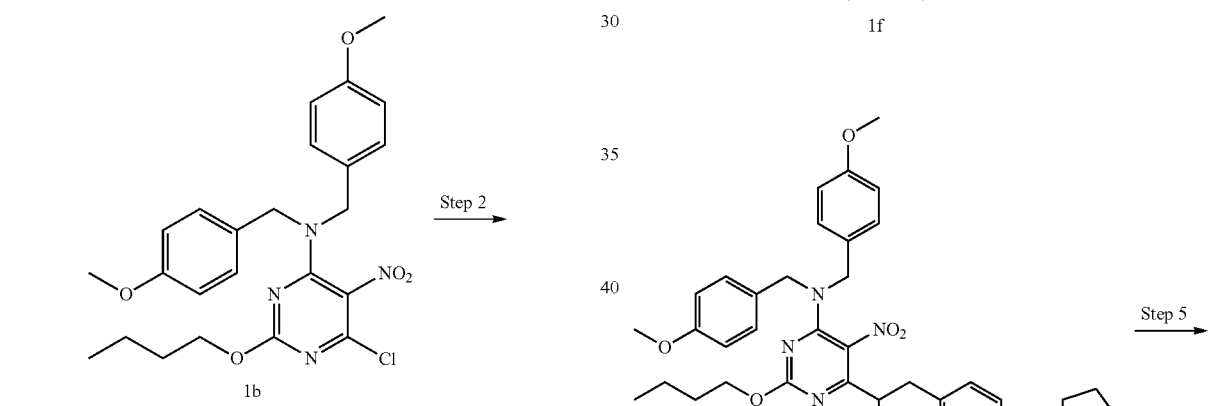
1d +
1f → Step 4
1g → Step 5
1h → Step 6

-continued

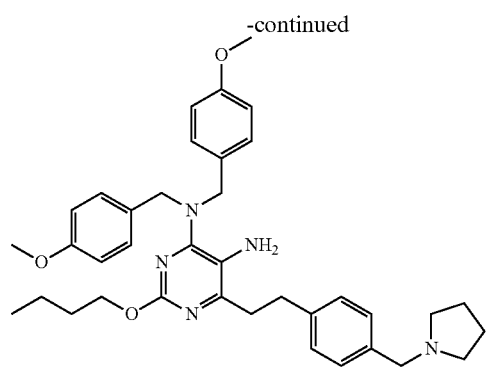

1i

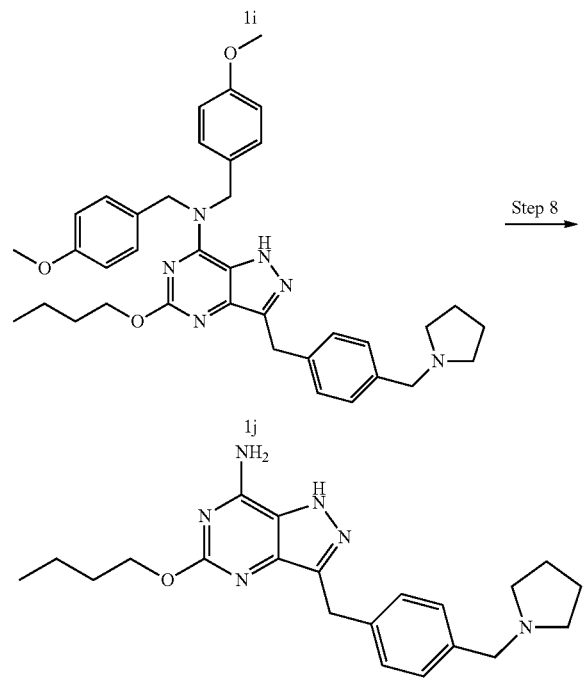

Step 1

2-Butoxy-6-chloro-N,N-bis(4-methoxybenzyl)-5-nitropyrimidin-4-amine 1b

2-Butoxy-4,6-dichloro-5-nitropyrimidine 1a (4.62 g, 17.43 mmol, prepared according to the known method disclosed in *Journal of Medicinal Chemistry,* 2012, 55(23), 10387-10404) was dissolved in tetrahydrofuran (50 mL), and triethylamine (2.64 g, 26.14 mmol) and N,N-bis(4-methoxybenzyl)amine (4.49 g, 17.43 mmol) were added therein in turn, and then the resulting mixture was stirred at room temperature for 4 hours. The reaction solution was concentrated under reduced pressure and the residue was purified by eluting system A using CombiFlash rapid preparation to give the title product 1b (6.20 g), 73.8% yield.

MS m/z (ESI): 487.5 [M+1].

Step 2

Diethyl 2-(6-(bis(4-methoxybenzyl)amino)-2-butoxy-5-nitropyrimidin-4-yl)malonate 1c The compound 1b (1.84 g, 3.78 mmol) was dissolved in acetone (60 mL). After cooling to 0° C., diethyl malonate (0.91 g, 5.68 mmol) and sodium hydroxide (0.52 g, 13 mmol) were added therein, and then water (1.2 mL) was slowly added dropwise. The reaction solution was stirred at room temperature for 2 hours and then water (100 mL) was added, and then acetic acid was added dropwise to pH 8. The mixture was extracted with ethyl acetate (70 mL×3) and the organic phase was combined, and washed with saturated sodium chloride solution (50 mL), dried over anhydrous sodium sulfate and filtered. The filtrate was concentrated under reduced pressure and the residue was purified by eluting system A using Silica gel column chromatography to give the title product 1c (2.3 g), 100% yield.

MS m/z (ESI): 611.3 [M+1].

Step 3

Ethyl 2-(6-(bis(4-methoxybenzyl)amino)-2-butoxy-5-nitropyrimidin-4-yl)acetate 1d The compound 1c (1.5 g, 2.46 mmol) and sodium chloride (0.57 g, 9.83 mmol) were dissolved in a mixed solvent of dimethyl sulfoxide and water (V/V=5:1, 24 mL), and the mixture was warmed to 160° C. and stirred for 2 hours. The reaction solution was cooled to room temperature and added with water (40 mL), extracted with ethyl acetate (100 mL) and the organic phase was washed with water (20 mL×3), dried over anhydrous sodium sulfate and filtered. The filtrate was concentrated under reduced pressure and the residue was purified by eluting system A using Silica gel column chromatography to give the title product 1d (660 mg), 47.39% yield.

MS m/z (ESI): 539.3 [M+1]

Step 4

Ethyl 2-(6-(Bis(4-methoxybenzyl)amino)-2-butoxy-5-nitropyrimidin-4-yl)-3-(4-(pyrrolidin-1-ylmethyl)phenyl)propanoate 1g The compound 1d (700 mg, 1.3 mmol) was dissolved in N,N-dimethylformamide (10 mL). After cooling to 0° C., sodium hydrogen (155.96 mg, 3.9 mmol) was added therein and stirred for 30 minutes. 1-(4-(Chloromethyl)benzyl)pyrrolidine 1f (408.86 mg, 1.95 mmol, prepared according to the known method disclosed in the patent application "WO2002012224") was added, and then the reaction mixture was heated to 100° C. and stirred for 2 hours. The reaction mixture was cooled to room temperature, and added with saturated ammonium chloride solution (30 mL), extracted with ethyl acetate (100 mL) and the organic phase was dried over anhydrous sodium sulfate and filtered. The filtrate was concentrated under reduced pressure and the residue was purified by eluting system A using Silica gel column chromatography to give the title product 1g (350 mg), 37.83% yield.

MS m/z (ESI): 712.3 [M+1]

Step 5

2-Butoxy-N,N-bis(4-methoxybenzyl)-5-nitro-6-(4-(pyrrolidin-1-ylmethyl)phenethyl)pyrimidin-4-amine 1h The compound 1g (120 mg, 168.58 μmol) was dissolved in a mixed solvent of tetrahydrofuran and water (V/V=2:1, 9 mL), and then lithium hydroxide (70.74 mg, 1.69 mmol) was added, then the reaction solution was heated to 60° C.

and stirred for 4 hours. The reaction solution was cooled to room temperature, and added with ethyl acetate, washed with saturated sodium chloride solution, and the organic phase was dried over anhydrous sodium sulfate and filtered. The filtrate was concentrated under reduced pressure to give the crude title product 1g (108 mg) which was used for the next step without further purification.

MS m/z (ESI): 640.3 [M+1]

Step 6

2-Butoxy-$N^4,N^4$-bis(4-methoxybenzyl)-6-(4-(pyrrolidin-1-ylmethyl)phenethyl)pyrimidine-4,5-diamine 1i The crude compound 1h (108 mg, 168.81 mol) was dissolved in acetic acid (5 mL), and zinc powder (165.57 mg, 2.53 mmol) was added therein, and the resulting mixture stirred for 1 hour. The reaction solution was filtered and the filtrate was concentrated under reduced pressure to give the crude title product 1i (90 mg) which was used for the next step without further purification.

MS m/z (ESI): 610.4 [M+1].

Step 7

5-Butoxy-N,N-bis(4-methoxybenzyl)-3-(4-(pyrrolidin-1-ylmethyl)benzyl)-1H-pyrazolo[4,3-d]pyrimidin-7-amine 1j The crude compound 1i (90 mg, 147.59 μmol) was dissolved in acetic acid (2 mL), and sodium nitrite (30.55 mg, 442.77 μmol) was added therein, and the reaction was stirred for 1 hour. Ethyl acetate (20 mL) was added into the reaction solution and washed with saturated sodium chloride solution (20 mL×3), dried over anhydrous sodium sulfate, filtered. The filtrate was concentrated under reduced pressure to give the crude title product 1j (91 mg) which was used for the next step without further purification.

MS m/z (ESI): 621.7 [M+1].

Step 8

5-Butoxy-3-(4-(pyrrolidin-1-ylmethyl)benzyl)-1H-pyrazolo[4,3-d]pyrimidin-7-amine 1

The crude compound 1j (90 mg, 144.98 μmol) was dissolved in trifluoroacetic acid (2 mL), and the mixture was heated to 60° C. and stirred for 48 hours. The reaction solution was concentrated under reduced pressure and the residue was purified by high performance liquid chromatography to give the crude title product 1 (7.1 mg), 12.87% yield.

MS m/z (ESI): 381.5 [M+1]

$^1$H NMR (400 MHz, CD$_3$OD) δ7.45 (d, 2H), 7.37 (d, 2H), 4.54 (t, 2H), 4.32 (s, 2H), 4.29 (s, 2H), 3.45 (s, 2H), 3.13 (s, 2H), 2.13 (s, 2H), 1.99 (s, 2H), 1.84-1.76 (m, 2H), 1.56-1.45 (m, 2H), 0.99 (t, 3H).

Biological Assay

Effect Embodiment 1: Determination of the Activation Effect of the Compound of the Present Application on Human TLR The activation effect of the compound of the present application on the hTLR7 protein expressed in HEK-Blue™ hTLR7 stably transfected cells and hTLR8 protein expressed in HEK-Blue™ hTLR8 stably transfected cells were determined by the following experimental method:

I. Experimental Materials and Instruments

DMEM (Gibco, 10564-029),
Fetal bovine serum (GIBCO, 10099),
Trypan blue solution (Sigma, T8154-100ML),
Flexstation 3 multi-function microplate reader (Molecular Devices),
HEK-Blue™ hTLR7 cell line (InvivoGen, hkb-hTLR7),
HEK-Blue™ hTLR8 cell line (InvivoGen, hkb-hTLR8),
HEK-Blue detection reagent (InvivoGen, hb-det3),
Phosphate buffer (PBS) pH 7.4 (Shanghai BasalMedia Technologies Co., Ltd., B320).

II. Experimental Procedures

The HEK-Blue assay medium was configured, HEK-Blue test dry powder was taken and 50 mL deendotoxin water were added to dissolve, then the resulting mixture was placed into the 37° C. incubator, and then filtered aseptically 10 minutes later. The compound was first formulated into a 20 mM stock solution, and then it was diluted with pure DMSO to a maximum concentration of 6×10$^6$ nM and diluted by a 3-fold gradient for a total of 10 points.

The above-prepared compound was diluted 20-fold with a medium, and then 20 μL of the diluted compound were added to each well. HEK-Blue™ hTLR7 cells and HEK-Blue™ hTLR8 cells were taken separately, and the supernatant was removed first, then 2-5 mL pre-warmed PBS was added, placed in an incubator for 1-2 minutes, and the cells were gently pipetted, stained with trypan blue and counted. The cells were resuspended in HEK-Blue assay medium to a concentration of 2.2×10$^5$ cells/mL, and 180 μL cells were added to the above 96-well cell culture plate where 20 μL the drug had been added, and cultured at 37° C. for 6-16 hours.

The microplate reader reads at a wavelength of 620 nm. The corresponding OD value was obtained, and the EC$_{50}$ value of the drug was calculated by Graphpad Prism. The activation effect of the compound of the present application and the control compound (prepared by the method of embodiment 21 of WO2016023511) on human TLR7 and TLR8 were determined by the above test, and the measured EC$_{50}$ values were as shown in Table 1.

TABLE 1

| EC$_{50}$ values of the compound of the present application and the control compound on human TLR7 and TLR8 | | |
|---|---|---|
| Embodiment No. | EC$_{50}$(TLR7)/nM | EC$_{50}$(TLR8)/nM |
| 1 | 53 | 5223 |
| Embodiment 21 of WO2016023511 | 243 | 12471 |

Conclusion: the compound of the present application demonstrates better activation on human TLR7 than the control compound embodiment 21 of WO2016023511, and the compound of the present application is more selective for TLR7 activation compared with the activation on human TLR8.

Effect Embodiment 2: Determination of the Ability of the Compound of the Present Application to Stimulate the Secretion of IFN-α from Peripheral Blood Mononuclear Cells (PBMC)

The ability of the compound of the present application to stimulate the secretion of IFN-α from PBMC was determined by the following experimental method:

I. Experimental Materials and Instruments
RPMI 1640 (Invitrogen, 11875),
FBS (Gibco, 10099-141),
Ficoll-Paque PREMIUM (GE, 17-5442-02),
Trypan blue solution (Sigma, T8154-100ML),
SepMate™-50 (Stemcell, 15460),
Bright-Line™ Blood Cell Counter (Sigma, Z359629-1EA),
96-well flat bottom plate (Corning, 3599),
96-well v backplane (Corning, 3894),
Human IFN-α kit (cisbio, 6FHIFPEB),
PHERAStar Multi-Function Microplate Reader (BMG, PHERAStar).

II. Experimental Procedures

Compounds were diluted in pure DMSO at a maximum concentration of 5 mM in 4-fold gradients for a total of 9 points. Then 4 μL of the compound were taken and added to 196 μL of RMPI 1640 medium containing 10% FBS and mixed. 50 μL per well were taken and added into a new 96-well cell culture plate.

All reagents were equilibrated to room temperature, and a 250 mL culture flask was taken and 60 mL blood and PBS+2% FBS were added therein, and the mixture was gently diluted by pipetting. 50 mL PBMC separation tube SepMate™-50 was taken and 15 mL lymphocyte separation solution Ficoll-Paque PREMIUM were added, and then 30 mL diluted blood were added and centrifuged at 1200 g for 10 minutes at room temperature. The supernatant was taken, and then centrifuged at 300 g for 8 minutes. The cells were resuspend with RMPI 1640 medium containing 10% FBS and counted, adjusted the amount of PBMC to $3.33 \times 10^6$ cells/mL, and 150 μL were taken and added to the cell culture plate to which the compound had been added, and cultured at 37° C. in a 5.0% $CO_2$ incubator for 24 hours.

The cell culture plate was placed in a centrifuge, centrifuged at 1200 rpm for 10 minutes at room temperature. 150 μL the supernatant were taken out per well. The reagent in the human IFN-α kit was firstly equilibrated to normal temperature, and anti-IFN-α-$Eu^{3+}$-Cryptate conjugate and anti-IFN-α-d2-conjugate were prepared according to the kit instructions in the dark, the conjugates were both mixed with a conjugate buffer at a ratio of 1:40. Then, 16 μL of the supernatant obtained by centrifugation were added into each well. Then, 2 μL of the anti-IFN-α-$Eu^{3+}$-Cryptate conjugate and the anti-IFN-α-d2-conjugate were added to each well, and the mixture was shaken and incubated at room temperature for 3 hours in the dark.

It was read in the HTRF mode on the PHERAStar. The lowest drug concentration that stimulated and produced the cytokine level at least 3 times of a minimum detection limit was defined as the MEC (Minimal Effective Concentration) value of the compound in the cytokine stimulation test.

The ability of the compound of the present application and the control compound (prepared by the method of embodiment 21 of WO2016023511) to stimulate the secretion of IFN-α from PBMC were determined by the above test, and the measured MEC values were as shown in Table 2.

TABLE 2 the MEC of the compound of the present application and the control compound to stimulate the secretion of IFN-α from PBMC

| Embodiment No. | MEC (nM) |
|---|---|
| 1 | 0.28 |
| Embodiment 21 of WO2016023511 | 5.5 |

Conclusion: based on the data of the activity of stimulating the secretion of IFN-α from PBMC, the compound of the present application demonstrates a smaller MEC value than that of the control compound embodiment 21 of WO2016023511, and was able to cause IFN-α release better.

Effect Embodiment 3: Inhibition of the Enzymatic Activity of the Compound of the Present Application Against the Midazolam Metabolite Site on Human Liver Microsome CYP3A4

The enzymatic activity of the compound of the present application against the Midazolam metabolite site on human liver microsome CYP3A4 was determined by the following experimental method:

I. Experimental Materials and Instruments
Phosphate buffer (PBS),
NADPH (Sigma N-1630),
Human liver microsomes (Corning Gentest),
ABI QTrap 4000 LC/MS (AB Sciex),
Inertsil C8-3 column, 4.6×50 mnm, 5 μm (American Dikma Company),
CYP probe substrate (15 μM Midazolam, SIGMA UC429) and positive control inhibitor (Ketoconazole, SIGMA K1003).

II. Experimental Procedures 100 mM PBS buffer was configured, and 2.5 mg/mL microsome solution and 5 mM NADPH solution were prepared with this buffer, and the 5× concentration compound working solution was diluted with PBS (150, 50, 15, 5, 1.5, 0.15, 0.015, 0 μM). The 5× concentration of Ketoconazole working solution (150, 50, 15, 5, 1.5, 0.15, 0.015, 0 μM) was diluted with PBS. Midazolam working solution was diluted to a concentration of 15 μM with PBS.

20 μL each of 2.5 mg/mL microsome solution, 15 μM Midazolam working solution, $MgCl_2$ solution and compound working solution (150, 50, 15, 5, 1.5, 0.15, 0.015, 0 μM, each concentration was setted differently reaction system) were taken and mixed evenly. The compound was replaced with the same concentration of Ketoconazole at the positive control group. At the same time, 5 mM NADPH solution was pre-incubated for 5 minutes at 37° C. After 5 minutes, 20 μL NADPH were added into the wells, and the reaction was started and incubated for 30 minutes. All samples were incubated for two samples. After 30 minutes, 250 μL internal standard-containing acetonitrile were added to all samples, mixed, shaken at 800 rpm for 10 minutes, and then centrifuged at 3700 rpm for 10 minutes. 80 μL the supernatant were taken and transferred to LC-MS/MS for analysis.

The $IC_{50}$ values of the drug for the Midazolam metabolic site on CYP3A4 calculated by Graphpad Prism were as shown in Table 3.

TABLE 3

The $IC_{50}$ values of the compound of the the present application and the control compound embodiment 21 of WO2016023511 for the midazolam metabolic site on CYP3A4

| Embodiment No. | $IC_{50}$ (μM) |
|---|---|
| 1 | 16.7 |
| Embodiment 21 of WO2016023511 | 1.02 |

Conclusion: the compound of the present application has no inhibitory effect on the Midazolam metabolic site of human liver microsome CYP3A4, suggesting that no metabolic drug interaction based on CYP3A4 metabolizing the midazolam metabolite site occurred, and demonstrates better safety compared with the control compound embodiment 21 of WO2016023511.

Effect Embodiment 4: The Inhibitory Effect on the Enzymatic Activity of the Compound of the Present Application Against Human Liver Microsome CYP2D6

The enzymatic activity of the compound of the present application against human liver microsome CYP2D6 was determined by the following experimental method:

I. Experimental Materials and Instruments
Phosphate buffer (PBS),
NADPH (Sigma N-1630),
Human liver microsomes (Corning Gentest),
ABI QTrap 4000 LC/MS (AB Sciex),
Inertsil C8-3 column, 4.6×50 mm, 5 μm (American Dikma Company),
CYP probe substrate (20 μM Dextromethorphan, SIGMA Q0750) and positive control inhibitor (Quinidine, SIGMA D9684).

II. Experimental Procedures 100 mM PBS buffer was configured, and 2.5 mg/mL microsome solution and 5 mM NADPH solution were prepared with this buffer, and the 5× concentration compound working solution was diluted with PBS (150, 50, 15, 5, 1.5, 0.15, 0.015, 0 μM). The 5× concentration of Quinidine working solution (150, 50, 15, 5, 1.5, 0.15, 0.015, 0 μM) was diluted with PBS. Dextromethorphan working solution was diluted to a concentration of 20 μM with PBS.

20 μL each of 2.5 mg/mL microsome solution, 20 μM Dextromethorphan working solution, $MgCl_2$ solution and compound working solution (150, 50, 15, 5, 1.5, 0.15, 0.015, 0 μM, each concentration was setted differently reaction system) were taken and mixed evenly. The compound was replaced with the same concentration of Quinidine at the positive control group. At the same time, 5 mM NADPH solution was pre-incubated for 5 minutes at 37° C. After 5 minutes, 20 μL NADPH were added into the wells, and the reaction was started and incubated for 30 minutes. All samples were incubated for two samples. After 30 minutes, 250 μL internal standard-containing acetonitrile were added to all samples, mixed, shaken at 800 rpm for 10 minutes, and then centrifuged at 3700 rpm for 10 minutes. 80 μL the supernatant were taken and transferred to LC-MS/MS for analysis.

The $IC_{50}$ values of the drug for the metabolic site on CYP2D6 calculated by Graphpad Prism were as shown in Table.

TABLE 4

The $IC_{50}$ values of the compound of the present application and the control compound embodiment 21 of WO2016023511 for the metabolic site on CYP2D6

| Embodiment No. | $IC_{50}$(μM) |
| --- | --- |
| 1 | >30 |
| Embodiment 21 of WO2016023511 | 5.3 |

Conclusion: the compound of the present application has no inhibitory effect against CYP2D6, suggesting that no metabolic drug interaction based on CYP2D6 occurred, and demonstrates better safety compared with the control compound embodiment 21 of WO2016023511.

Effect Embodiment 5: Blocking Effect of the Compound of the Present Application on hERG Potassium Current The blocking effect of the compound of the present application on hERG potassium current was tested using an automatic patch-clamp on a stable cell line transfected with hERG potassium channels.

I. Experimental Materials and Instruments
1. Experimental Materials:

| Name of reagent | Supply company | Code |
| --- | --- | --- |
| FBS | GIBCO | 10099 |
| Sodium acetone solution | sigma | S8636-100ML |
| MEM Non-essential amino acid solution (100×) | sigma | M7145-100ML |
| G418 Sulfate | Enzo | ALX-380-013-G005 |
| MEM | Hyclone | SH30024.01B |
| hERG cDNA | Origene | — |

2. Experimental Equipments:

| Experimental equipment | Supply company | Code |
| --- | --- | --- |
| Patchliner 4 channel | nanion | 2-03-03100-002 |
| Patchliner Cleaning Station | nanion | 2-02-03201-005 |
| Patchliner cell bank | nanion | 2-02-03105-000 |
| Elektrodenchloridierer Patchliner | nanion | 3-02-03533-000 |
| HEAK EPC10 Patch clamp Amplifier | nanion | 1-01-10012-000 |
| osmotic pressure tester | Gonoter | Gonoter 030 |
| pH meter | Mettle Toledo | FE20 |

II. Automatic Patch-Clamp Experimental Procedure

The HEK293-hERG stable cell line was subcultured at a density of 1:4 in MEM/EBSS medium (10% FBS, 400 μg/mL G418, 1% MEM non-essential amino acid solution (100×), 1% sodium pyruvate solution) and cultured within 48-72 hours for automatic patch-clamp experiments. On the day of the experiment, the cells were digested with 0.25% trypsin, collected by centrifugation and resuspended with extracellular fluid (140 mM NaCl, 4 mM KCl, 1 mM $MgCl_2$, 2 mM $CaCl_2$, 5 mM MD glucose monohydrate, 10 mM Hepes, pH 7.4, 298 mOsmol) to give a cell suspension. The cell suspension was placed on the cell bank of the Patchliner instrument, the Patchliner instrument used a negative pressure controller to apply the cells to the chip (NPC-16), and the negative pressure attracted individual cells to the wells of the chip. When the whole cell mode was formed, the instrument got the hERG current according to the set hERG current voltage program, and then the instrument automatically perfused the compound from low to high concentration. The currents at each concentration of the compound and the blank control current were analyzed by HEAK Patchmaster, HEAK EPC 10 patch clamp amplifiers (Nanion) and Pathlinersoftware and data analysis software provided by Pathcontrol HTsoftware.

III. Experimental Results

Blocking effect of the compound of the present application on hERG potassium current was determined by the above experimental method, and the $IC_{50}$ values were as shown in Table 5.

TABLE 5

| | |
|---|---|
| IC$_{50}$ values of blocking effect of the compound of the present application and the control compound embodiment 21 of WO2016023511 on hERG potassium current | |
| Embodiment No. | IC$_{50}$ (μM) |
| 1 | >30 |
| Embodiment 21 of WO2016023511 | 3.6 |

Conclusion: the compound of the present application has a weak inhibitory effect on hERG, and could reduce side effects caused by the hERG pathway, and demonstrates better safety compared with the control compound embodiment 21 of WO2016023511.

What is claimed is:

1. A compound of formula (I):

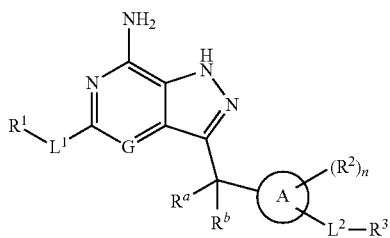

or a tautomer, a mesomer, a racemate, an enantiomer, a diastereomer thereof, or a mixture thereof, or a pharmaceutically acceptable salt thereof, wherein, ring A is selected from the group consisting of cycloalkyl, aryl and heteroaryl;

G is N or CR$^4$;

L$^1$ is selected from the group consisting of —NR$^5$—, —O—, —C(O)—, —S(O)$_m$—, —N(R$^5$)C(O)—, —C(O)N(R$^5$)—, —N(R$^5$)S(O)$_2$—, —S(O)$_2$N(R$^5$)— and a covalent bond;

R$^1$ is selected from the group consisting of hydrogen atom, alkyl, haloalkyl, alkenyl, alkynyl, cycloalkyl, heterocyclyl, aryl and heteroaryl, wherein each of the alkyl, alkenyl, alkynyl, cycloalkyl, heterocyclyl, aryl and heteroaryl is independently and optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl and heteroaryl;

each R$^2$ is identical or different, and each is independently selected from the group consisting of hydrogen atom, halogen, alkyl, alkoxy, haloalkyl, hydroxy, hydroxyalkyl, cyano, amino, nitro, cycloalkyl, heterocyclyl, aryl, heteroaryl, —C(O)R$^6$, —C(O)OR$^6$, —S(O)$_m$R$^6$, —NR$^7$R$^8$ and —C(O)NR$^7$R$^8$, wherein each of the alkyl, cycloalkyl, heterocyclyl, aryl and heteroaryl is independently and optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl and heteroaryl;

L$^2$ is alkylene or a covalent bond, wherein the alkylene is optionally substituted by one or more substituents selected from the group consisting of halogen, alkyl, alkoxy, haloalkyl, hydroxy, hydroxyalkyl, cyano, amino, nitro, cycloalkyl and heterocyclyl;

R$^3$ is selected from the group consisting of hydrogen atom, alkyl, alkoxy, halogen, haloalkyl, hydroxy, hydroxyalkyl, cyano, amino, nitro, cycloalkyl, heterocyclyl, aryl, heteroaryl, —C(O)R$^6$, —C(O)OR$^6$, —S(O)$_m$R$^6$, —NR$^7$R$^8$ and —C(O)NR$^7$R$^8$, wherein each of the cycloalkyl, heterocyclyl, aryl and heteroaryl is independently and optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —C(O)R$^6$, —C(O)OR$^6$, —S(O)$_m$R$^6$, —NR$^7$R$^8$ and —C(O)NR$^7$R$^8$;

R$^a$ and R$^b$ are identical or different, and each is independently selected from the group consisting of hydrogen atom, halogen, alkyl, alkoxy, haloalkyl, hydroxy, hydroxyalkyl, cyano, amino, nitro, cycloalkyl, heterocyclyl, aryl and heteroaryl;

R$^4$ is selected from the group consisting of hydrogen atom, halogen, alkyl, alkoxy, haloalkyl, hydroxy, hydroxyalkyl, cyano, amino, nitro, cycloalkyl, heterocyclyl, aryl and heteroaryl;

R$^5$ is selected from the group consisting of hydrogen atom, alkyl, haloalkyl, cycloalkyl, heterocyclyl, aryl and heteroaryl;

R$^6$ is selected from the group consisting of hydrogen atom, alkyl, haloalkyl, amino, hydroxy, hydroxyalkyl, cycloalkyl, heterocyclyl, aryl and heteroaryl;

R$^7$ and R$^8$ are identical or different, and each is independently selected from the group consisting of hydrogen atom, alkyl, haloalkyl, cycloalkyl, heterocyclyl, aryl and heteroaryl, wherein each of the alkyl, cycloalkyl, heterocyclyl, aryl and heteroaryl is independently and optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

or, R$^7$ and R$^8$ are linked together with the attached nitrogen atom to form heterocyclyl, wherein, except the one nitrogen atom, the heterocyclyl contains one or two identical or different heteroatoms selected from the group consisting of N, O and S, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

n is 0, 1, 2, 3 or 4; and m is 0, 1 or 2.

2. The compound according to claim 1, being a compound of formula (II):

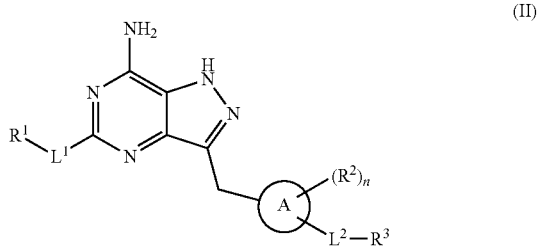

or a tautomer, a mesomer, a racemate, an enantiomer, a diastereomer thereof, or a mixture thereof, or a pharmaceutically acceptable salt thereof, wherein
the ring A, $L^1$, $L^2$, $R^1$, $R^2$, $R^3$ and n are as defined in claim 1.

3. The compound according to claim 1, wherein the ring A is phenyl or pyridyl.

4. The compound according to claim 1, being a compound of formula (III):

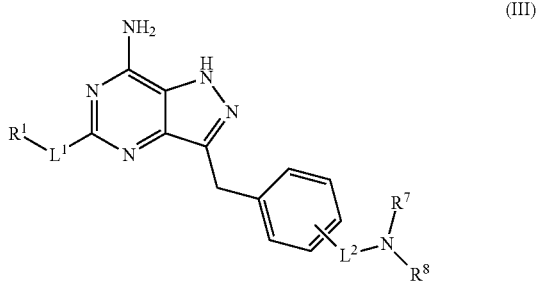

(III)

or a tautomer, a mesomer, a racemate, an enantiomer, a diastereomer thereof, or a mixture thereof, or a pharmaceutically acceptable salt thereof,
wherein,
$R^7$ and $R^8$ are linked together with the attached nitrogen atom to form heterocyclyl, wherein, except the one nitrogen atom, the heterocyclyl contains one or two identical or different heteroatoms selected from the group consisting of N, O and S, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl; and
$L^1$, $L^2$, and $R^1$ are as defined in claim 1.

5. The compound according to claim 1, wherein $L^1$ is —O—.

6. The compound according to claim 1, wherein $R^1$ is alkyl.

7. The compound according to claim 1, wherein $L^2$ is alkylene.

8. A compound of formula:

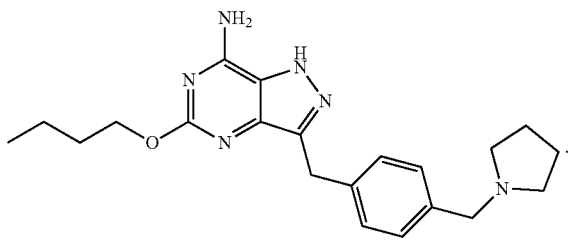 [SMILES: CCCCOc1nc(N)c2[nH]cc(Cc3ccc(CN4CCCC4)cc3)c2n1]

1

9. A compound of formula (IA):

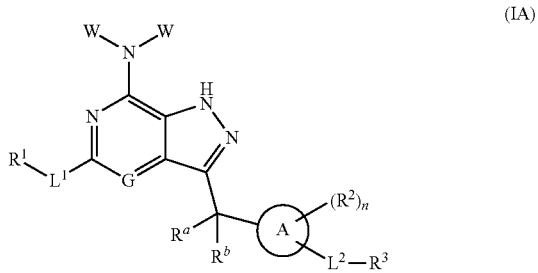

(IA)

or a tautomer, a mesomer, a racemate, an enantiomer, a diastereomer thereof, or a mixture thereof, or a pharmaceutically acceptable salt thereof, wherein,
W is amino protecting group;
ring A is selected from the group consisting of cycloalkyl, aryl and heteroaryl;
G is N or $CR^4$;
$L^1$ is selected from the group consisting of —$NR^5$—, —O—, —C(O)—, —S(O)$_m$—, —N($R^5$)C(O)—, —C(O)N($R^5$)—, —N($R^5$)S(O)$_2$—, —S(O)$_2$N($R^5$)— and a covalent bond;
$R^1$ is selected from the group consisting of hydrogen atom, alkyl, haloalkyl, alkenyl, alkynyl, cycloalkyl, heterocyclyl, aryl and heteroaryl, wherein each of the alkyl, alkenyl, alkynyl, cycloalkyl, heterocyclyl, aryl and heteroaryl is independently and optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl and heteroaryl;
each $R^2$ is identical or different, and each is independently selected from the group consisting of hydrogen atom, halogen, alkyl, alkoxy, haloalkyl, hydroxy, hydroxyalkyl, cyano, amino, nitro, cycloalkyl, heterocyclyl, aryl, heteroaryl, —C(O)$R^6$, —C(O)O$R^6$, —S(O)$_m R^6$, —$NR^7 R^8$ and —C(O)$NR^7 R^8$, wherein each of the alkyl, cycloalkyl, heterocyclyl, aryl and heteroaryl is independently and optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl and heteroaryl;
$L^2$ is alkylene or a covalent bond, wherein the alkylene is optionally substituted by one or more substituents selected from the group consisting of halogen, alkyl, alkoxy, haloalkyl, hydroxy, hydroxyalkyl, cyano, amino, nitro, cycloalkyl and heterocyclyl;
$R^3$ is selected from the group consisting of hydrogen atom, alkyl, alkoxy, halogen, haloalkyl, hydroxy, hydroxyalkyl, cyano, amino, nitro, cycloalkyl, heterocyclyl, aryl, heteroaryl, —C(O)$R^6$, —C(O)O$R^6$, —S(O)$_m R^6$, —$NR^7 R^8$ and —C(O)$NR^7 R^8$, wherein each of the cycloalkyl, heterocyclyl, aryl and heteroaryl is independently and optionally substituted by one or more substituents selected from the group consisting of alkyl, alkoxy, halogen, haloalkyl, hydroxy, hydroxyalkyl, cyano, amino, nitro, cycloalkyl, heterocyclyl, aryl, heteroaryl, —C(O)$R^6$, —C(O)O$R^6$, —S(O)$_m R^6$, —$NR^7 R^8$ and —C(O)$NR^7 R^8$;
$R^a$ and $R^b$ are identical or different, and each is independently selected from the group consisting of hydrogen atom, halogen, alkyl, alkoxy, haloalkyl, hydroxy, hydroxyalkyl, cyano, amino, nitro, cycloalkyl, heterocyclyl, aryl and heteroaryl;
$R^4$ is selected from the group consisting of hydrogen atom, halogen, alkyl, alkoxy, haloalkyl, hydroxy, hydroxyalkyl, cyano, amino, nitro, cycloalkyl, heterocyclyl, aryl and heteroaryl;
$R^5$ is selected from the group consisting of hydrogen atom, alkyl, haloalkyl, cycloalkyl, heterocyclyl, aryl and heteroaryl;
$R^6$ is selected from the group consisting of hydrogen atom, alkyl, haloalkyl, amino, hydroxy, hydroxyalkyl, cycloalkyl, heterocyclyl, aryl and heteroaryl;
$R^7$ and $R^8$ are identical or different, and each is independently selected from the group consisting of hydrogen atom, alkyl, haloalkyl, cycloalkyl, heterocyclyl, aryl and heteroaryl, wherein each of the alkyl, cycloalkyl, heterocyclyl, aryl and heteroaryl is independently and optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

or, $R^7$ and $R^8$ are linked together with the attached nitrogen atom to form heterocyclyl, wherein, except the one nitrogen atom, the heterocyclyl contains one or two identical or different heteroatoms selected from the group consisting of N, O and S, and the heterocyclyl is optionally substituted by one or more substituents selected from the group consisting of alkyl, alkoxy, halogen, amino, cyano, nitro, hydroxy, hydroxyalkyl, cycloalkyl, heterocyclyl, aryl and heteroaryl;

n is 0, 1, 2, 3 or 4; and m is 0, 1 or 2.

10. The compound according to claim 9, being a compound of

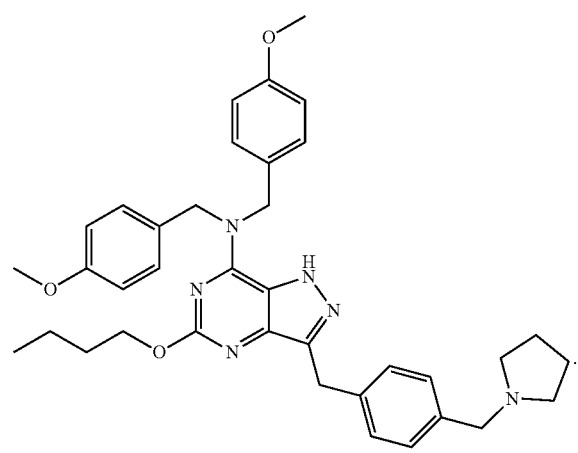

1j

11. A method for preparing the compound of formula (IA) according to claim 9, comprising:

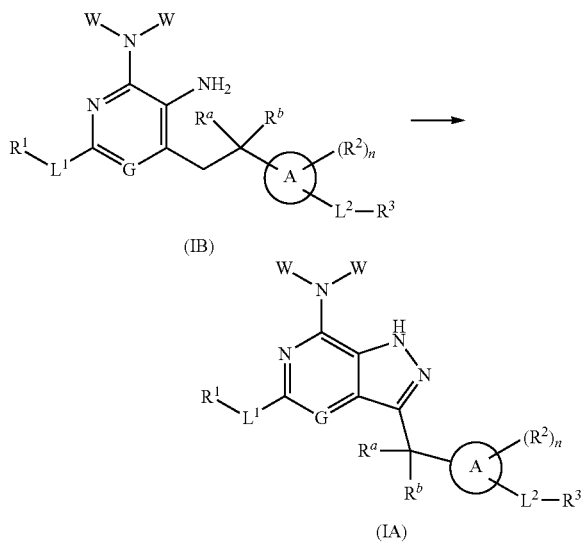

reacting a compound of formula (IB) with a nitrite salt to obtain the compound of formula (IA);

wherein,

W is amino protecting group; and the ring A, G, $L^1$, $L^2$, $R^1$, $R^2$, $R^3$, $R^a$, $R^b$ and n are as defined in claim 9.

12. A method for preparing the compound of formula (I) according to claim 1, comprising:

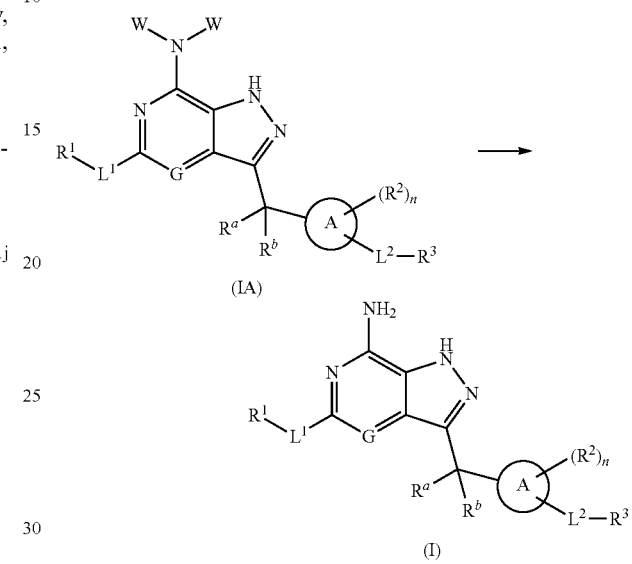

carrying out a de-protecting group reaction on a compound of formula (IA) to obtain the compound of formula (I);

wherein,

W is amino protecting group; and the ring A, G, $L^1$, $L^2$, $R^1$, $R^2$, $R^3$, $R^a$, $R^b$ and n are as defined in claim 1.

13. A pharmaceutical composition, comprising a therapeutically effective amount of the compound according to claim 1, and one or more pharmaceutically acceptable carriers, diluents or excipients.

14. A method of treating an infection caused by viruses in a patient in need thereof, the method comprising administering to the patient a therapeutically effective amount of the pharmaceutical composition according to claim 13, wherein the virus is selected from the group consisting of dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, Zika virus, HIV, HBV, HCV, HPV, RSV, SARS and influenza virus.

15. A method of treating a cancer in a patient in need thereof, the method comprising administering to the patient a therapeutically effective amount of the pharmaceutical composition according to claim 13, wherein the cancer is selected from the group consisting of melanoma, non-small cell lung cancer, hepatocellular carcinoma, basal cell carcinoma, renal cell carcinoma and myeloma.

* * * * *